US012657849B2

(12) United States Patent
Sakamoto et al.

(10) Patent No.: US 12,657,849 B2
(45) Date of Patent: Jun. 16, 2026

(54) 3D RECONSTRUCTION OF CROSS-SECTIONAL CUTTING PLANES IN IVUS IMAGES

(71) Applicant: TERUMO KABUSHIKI KAISHA, Tokyo (JP)

(72) Inventors: Yasukazu Sakamoto, Hiratsuka (JP); Katsuhiko Shimizu, Fujinomiya (JP); Hiroyuki Ishihara, Tokyo (JP); Clément Jacquet, Sakai (JP); Stephen Tchen, Sakai (JP); Thomas Henn, Sakai (JP); Ryosuke Saga, Osaka (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 21 days.

(21) Appl. No.: 18/190,566

(22) Filed: Mar. 27, 2023

(65) Prior Publication Data

US 2023/0252749 A1 Aug. 10, 2023

Related U.S. Application Data

(63) Continuation of application No. PCT/JP2021/035458, filed on Sep. 27, 2021.

(30) Foreign Application Priority Data

Sep. 29, 2020 (JP) .................................. 2020-164184

(51) Int. Cl.
*G06T 19/20* (2011.01)
*A61B 8/00* (2006.01)
*A61B 8/12* (2006.01)

(52) U.S. Cl.
CPC ................ *G06T 19/20* (2013.01); *A61B 8/12* (2013.01); *A61B 8/463* (2013.01); *A61B 8/466* (2013.01);

(Continued)

(58) Field of Classification Search
None
See application file for complete search history.

(56) References Cited

U.S. PATENT DOCUMENTS 6,251,072 B1 6/2001 Ladak et al.
6,385,332 B1 5/2002 Zahalka et al.
(Continued)

FOREIGN PATENT DOCUMENTS

JP H09-103432 A 4/1997
JP 2000316864 A 11/2000
(Continued)

OTHER PUBLICATIONS

Freeling et al., "Assessment of murine colorectal cancer by micro-ultrasound using three dimensional reconstruction and non-linear contrast imaging," (Nov. 30, 2016), Mol Ther Methods Clin Dev. 2016; 5: 16070. (Year: 2016).*

(Continued)

*Primary Examiner* — Keith M Raymond
*Assistant Examiner* — Ashish S. Jasani
(74) *Attorney, Agent, or Firm* — Buchanan Ingersoll & Rooney PC

(57) ABSTRACT

An image processing device for causing a display to display, as a three-dimensional image, three-dimensional data representing a biological tissue includes: a control unit configured to form, in the three-dimensional data, a cutting region exposing a lumen of the biological tissue in the three-dimensional image, and cause the display to display, together with the three-dimensional image, a two-dimensional image representing a cross section of the biological tissue and a region corresponding to the cutting region in the cross section.

18 Claims, 14 Drawing Sheets

(52) U.S. Cl.
CPC ........ *A61B 8/5207* (2013.01); *G06T 2210/41*
(2013.01); *G06T 2219/008* (2013.01); *G06T*
*2219/2012* (2013.01)

(56) References Cited

U.S. PATENT DOCUMENTS

| | | | | |
|---|---|---|---|---|
| 2006/0270928 | A1* | 11/2006 | Geiger .................... | G06T 19/20 |
| | | | | 600/407 |
| 2010/0215238 | A1 | 8/2010 | Lu et al. | |
| 2012/0065511 | A1* | 3/2012 | Jamello, III ........... | A61B 8/465 |
| | | | | 600/443 |
| 2014/0098099 | A1* | 4/2014 | Welford .................. | G06T 19/20 |
| | | | | 345/427 |
| 2016/0163048 | A1* | 6/2016 | Yee ........................ | A61B 6/032 |
| | | | | 382/131 |
| 2016/0381256 | A1* | 12/2016 | Aguirre-Valencia ........................ | |
| | | | | H04N 13/30 |
| | | | | 348/46 |
| 2019/0318484 | A1* | 10/2019 | Dougherty ................ | G06T 7/11 |
| 2021/0110597 | A1* | 4/2021 | Knoplioch .............. | G06T 15/08 |

FOREIGN PATENT DOCUMENTS

| | | | | |
|---|---|---|---|---|
| JP | 2002-143167 | A | 5/2002 | |
| KR | 101906944 | B1 * | 10/2018 | ........... G06T 11/003 |

OTHER PUBLICATIONS

Nain et al., "An Interactive Virtual Endoscopy Tool," (Sep. 2001), Presented at the Workshop on Interactive Medical Image Visualization and Analysis, IMIVA'01, satellite symposia of MICCAI, Utrecht, The Netherlands, Sep. 2001). (Year: 2001).*

International Search Report (PCT/ISA/210) with translation and Written Opinion (PCT/ISA/237) mailed on Dec. 14, 2021, by the Japan Patent Office as the International Searching Authority for International Application No. PCT/JP2021/035458. (9 pages).

Office Action (Notice of Reasons for Refusal) issued on Mar. 10, 2026, in corresponding Japanese Patent Application No. 2022-553969 and English translation of the Office Action. (12 pages).

* cited by examiner

*FIG. 2*

SETTING OF CUTTING REGION

☑ ACTIVATE

BASE ANGLE

OPENING ANGLE

☑ USE CENTROID

FIG. 3
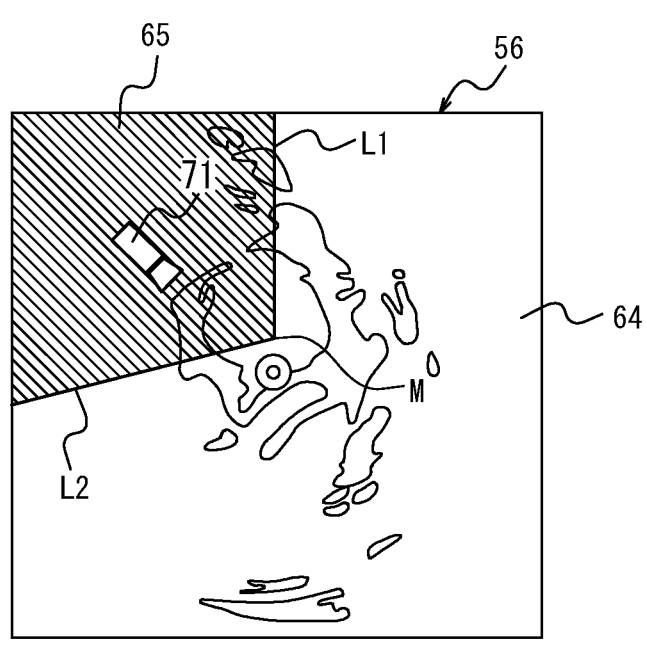
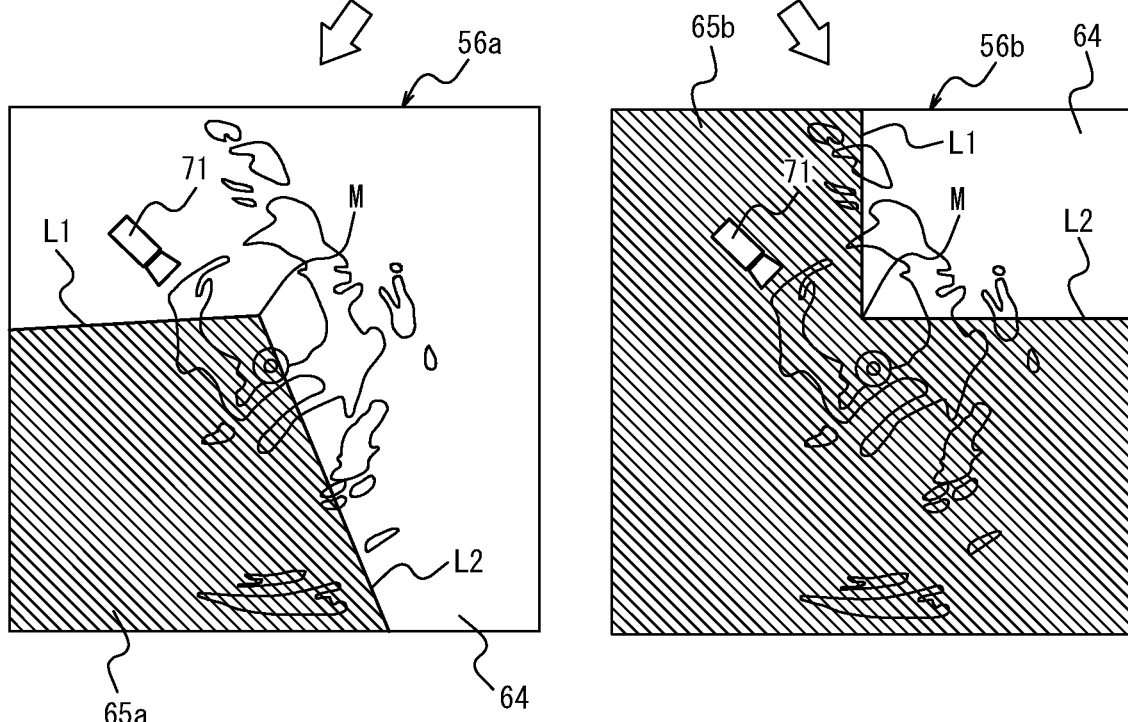

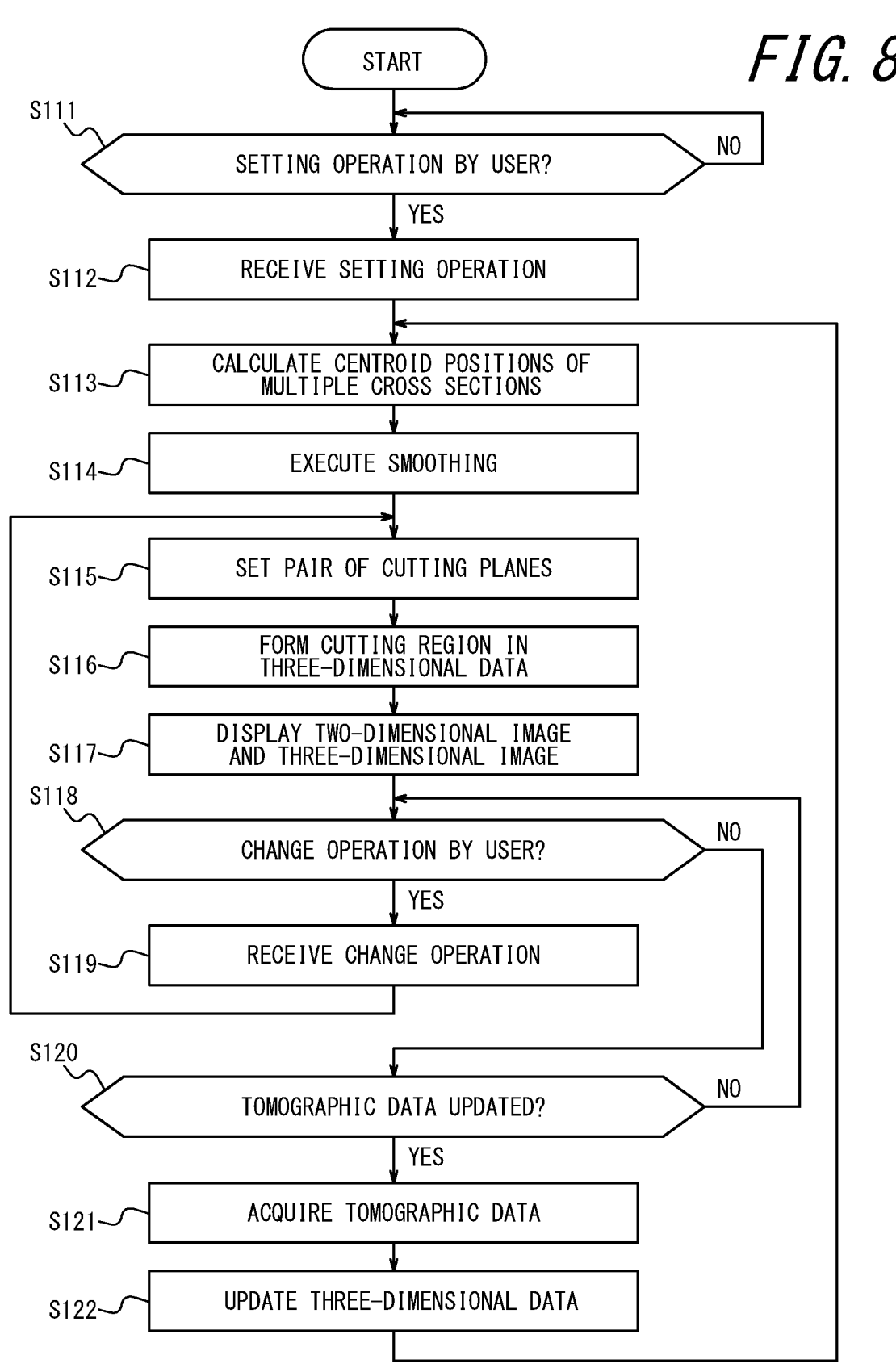

*FIG. 8*

START

S111 — SETTING OPERATION BY USER? — NO

YES

S112 — RECEIVE SETTING OPERATION

S113 — CALCULATE CENTROID POSITIONS OF MULTIPLE CROSS SECTIONS

S114 — EXECUTE SMOOTHING

S115 — SET PAIR OF CUTTING PLANES

S116 — FORM CUTTING REGION IN THREE-DIMENSIONAL DATA

S117 — DISPLAY TWO-DIMENSIONAL IMAGE AND THREE-DIMENSIONAL IMAGE

S118 — CHANGE OPERATION BY USER? — NO

YES

S119 — RECEIVE CHANGE OPERATION

S120 — TOMOGRAPHIC DATA UPDATED? — NO

YES

S121 — ACQUIRE TOMOGRAPHIC DATA

S122 — UPDATE THREE-DIMENSIONAL DATA

*FIG. 14*

SETTING OF CUTTING REGION

ACTIVATE

BASE ANGLE

OPENING ANGLE

USE CENTROID

3D RECONSTRUCTION OF CROSS-SECTIONAL CUTTING PLANES IN IVUS IMAGES

CROSS-REFERENCES TO RELATED APPLICATIONS

This application is a continuation of International Application No. PCT/JP2021/035458 filed on Sep. 27, 2021, which claims priority to Japanese Application No. 2020-164184 filed on Sep. 29, 2020, the entire contents of both of which is incorporated herein by reference.

TECHNOLOGICAL FIELD

The present disclosure generally relates to an image processing device, an image processing system, an image display method, and an image processing program.

BACKGROUND DISCUSSION

U.S. Patent Application Publication No. 2010/0215238 A1, U.S. Pat. Nos. 6,385,332 B, and 6,251,072 B disclose a technique of generating a three-dimensional image of a cardiac cavity or a blood vessel by using an ultrasound (US) image system.

A treatment using intravascular ultrasound (IVUS) is widely executed on regions such as cardiac cavity, cardiac blood vessel, and lower limb artery. The IVUS is a device or method for providing a two-dimensional image of a plane perpendicular to a long axis of a catheter.

At present, an operator needs to execute a treatment while reconstructing a three-dimensional structure by stacking two-dimensional images of IVUS in one's head, which causes a barrier particularly to young doctors or inexperienced doctors. In order to eliminate such a barrier, it is conceivable to automatically generate a three-dimensional image expressing a structure of a biological tissue such as a cardiac cavity or a blood vessel from the two-dimensional images of IVUS and to display the generated three-dimensional image toward the operator.

However, if the operator can see only an outer wall of the biological tissue in the three-dimensional image, the operator cannot perform a treatment for the inside of the biological tissue. Therefore, it is conceivable to cut out a part of the structure of the biological tissue in the three-dimensional image to see a lumen. At this time, it is required to confirm how a part of the structure of the biological tissue is cut out.

SUMMARY

The present disclosure is to indicate how a part of a structure of a biological tissue is cut out.

An image processing device according to one aspect of the present disclosure is an image processing device for causing a display to display, as a three-dimensional image, three-dimensional data representing a biological tissue. The image processing device includes: a control unit configured to form, in the three-dimensional data, a cutting region exposing a lumen of the biological tissue in the three-dimensional image, and cause the display to display, together with the three-dimensional image, a two-dimensional image representing a cross section of the biological tissue and a region corresponding to the cutting region in the cross section.

In one embodiment, the control unit is configured to receive an operation of setting the region corresponding to the cutting region on a cross-sectional image representing the cross section of the biological tissue, and form the cutting region in accordance with the set region.

In one embodiment, the control unit is configured to receive an operation of setting two straight lines extending from one point in the cross-sectional image as the operation of setting the region corresponding to the cutting region.

In one embodiment, the control unit is configured to receive an operation of designating a direction of one of the two straight lines and an angle formed by the two straight lines as the operation of setting the two straight lines.

In one embodiment, the control unit is configured to receive an operation of drawing the two straight lines on the cross-sectional image as the operation of setting the two straight lines.

In one embodiment, the one point is a centroid of the cross section of the biological tissue, and the control unit is configured to form the cutting region by setting, as cutting planes, two planes that intersect at a single line passing through centroids of cross sections of the biological tissue and that include the respective two straight lines.

In one embodiment, the control unit is configured to generate, as the two-dimensional image, an image in which the region corresponding to the cutting region is represented by a color different from a color of a remaining region.

In one embodiment, the control unit is configured to color, in the three-dimensional image, at least a voxel representing an inner surface of the biological tissue or a voxel that is adjacent to the voxel representing the inner surface and that represents the lumen among a first voxel group corresponding to the cross section represented by the two-dimensional image, in a manner of being distinguished from a second voxel group corresponding to another cross section of the biological tissue.

In one embodiment, the control unit is configured to color not only the first voxel group but also at least a voxel representing the inner surface or a voxel that is adjacent to the voxel representing the inner surface and that represents the lumen among a voxel group corresponding to a cross section adjacent to the cross section corresponding to the first voxel group, in a manner of being distinguished from a voxel group corresponding to another cross section of the biological tissue.

An image processing system according to one aspect of the present disclosure includes: the image processing device; and a probe including a sensor configured to acquire tomographic data of the biological tissue while moving through the lumen, in which the control unit is configured to generate the three-dimensional data based on the tomographic data acquired by the sensor.

In one embodiment, the image processing system further includes: the display.

An image display method according to one aspect of the present disclosure is an image display method for causing a display to display, as a three-dimensional image, three-dimensional data representing a biological tissue. The image display method includes: forming, by a computer, in the three-dimensional data, a cutting region exposing a lumen of the biological tissue in the three-dimensional image; and displaying, together with the three-dimensional image, a two-dimensional image representing a cross section of the biological tissue and a region corresponding to the cutting region in the cross section on the display.

A non-transitory computer readable medium storing an image processing program according to one aspect of the present disclosure when executed by a computer, causes a display to display, as a three-dimensional image, three-dimensional data representing a biological tissue, and performs processing comprising: forming, in the three-dimensional data, a cutting region exposing a lumen of the biological tissue in the three-dimensional image; and causing the display to display, together with the three-dimensional image, a two-dimensional image representing a cross section of the biological tissue and a region corresponding to the cutting region in the cross section.

According to the present disclosure, it is possible to show how a part of the structure of the biological tissue is cut out.

BRIEF DESCRIPTION OF THE DRAWINGS

FIG. 2 is a diagram showing an example of a screen displayed on a display by an image processing system according to the embodiment of the present disclosure.

FIG. 3 is a diagram showing an example of a two-dimensional image displayed on the display by the image processing system according to the embodiment of the present disclosure.

FIG. 8 is a flowchart illustrating an operation of the image processing system according to the embodiment of the present disclosure.

FIG. 14 is a diagram showing an example of a screen displayed on a display by an image processing system according to one modification of the embodiment of the present disclosure.

DETAILED DESCRIPTION

Figure 1:
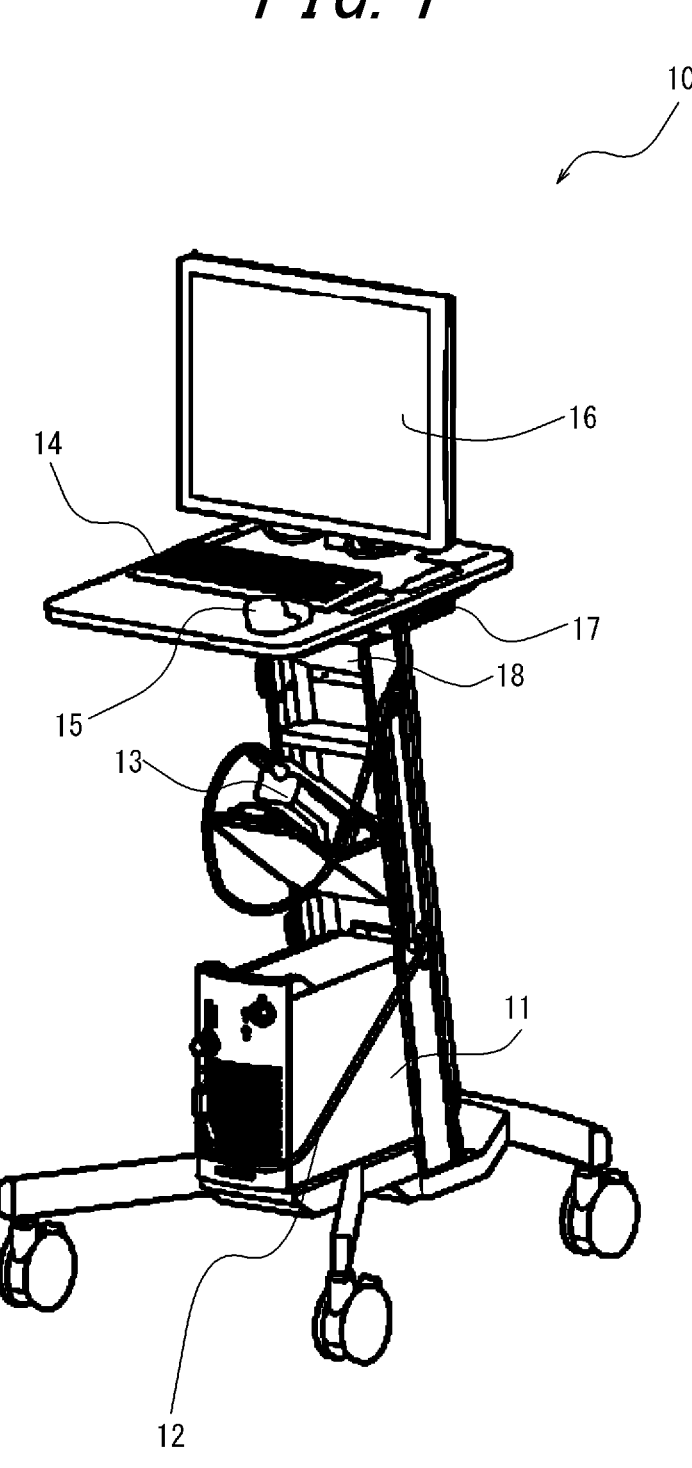
FIG. 1 is a perspective view of an image processing system according to an embodiment of the present disclosure.

Set forth below with reference to the accompanying drawings is a detailed description of embodiments of an image processing device, an image processing system, an image display method, and an image processing program.

In the drawings, the same or corresponding parts are denoted by the same reference numerals. In the description of the present embodiment, the description of the same or corresponding parts will be omitted or simplified as appropriate.

An outline of the present embodiment will be described with reference to FIGS. 1 to 4 and FIG. 6.

Figure 2:
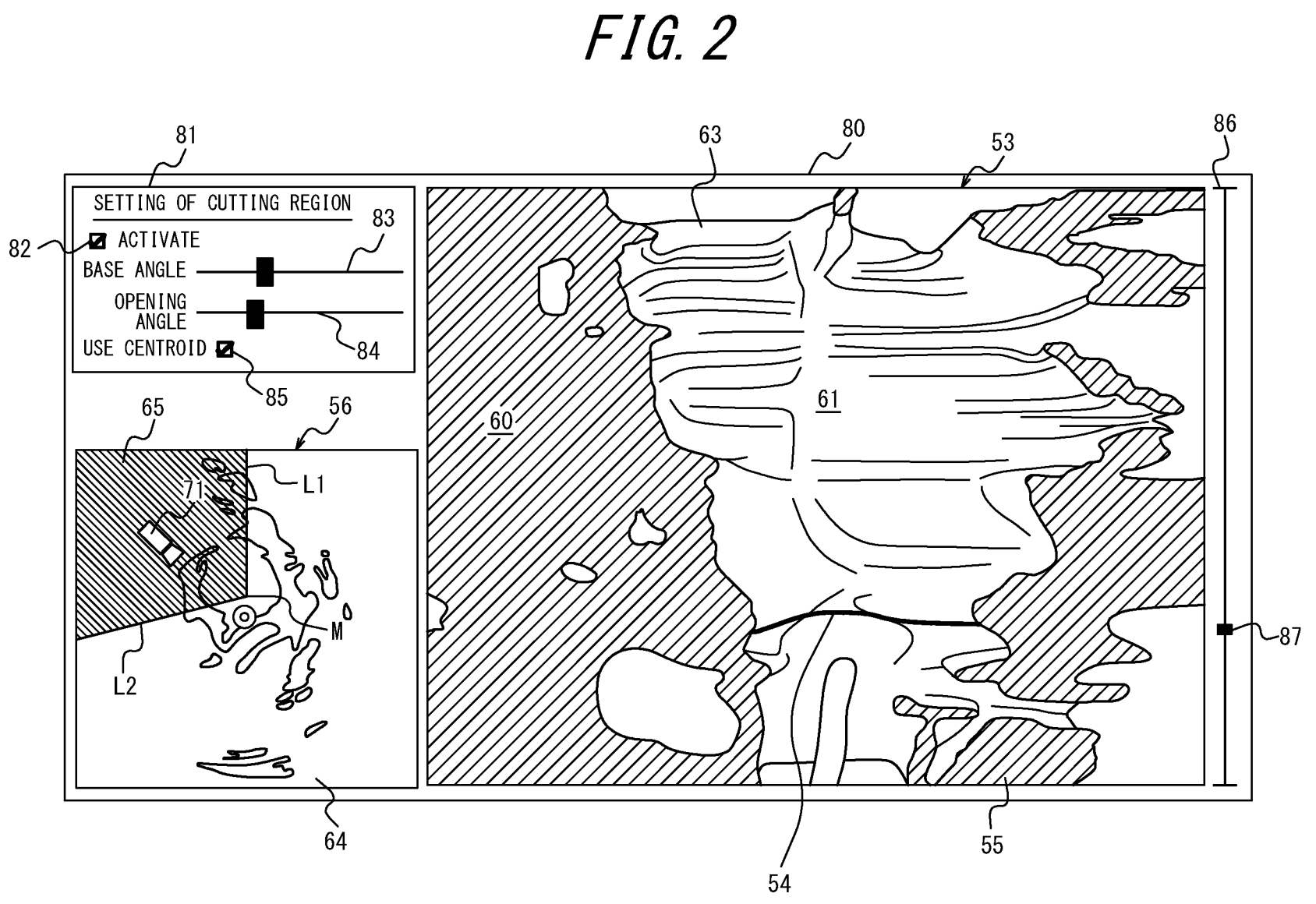
Figure 4:
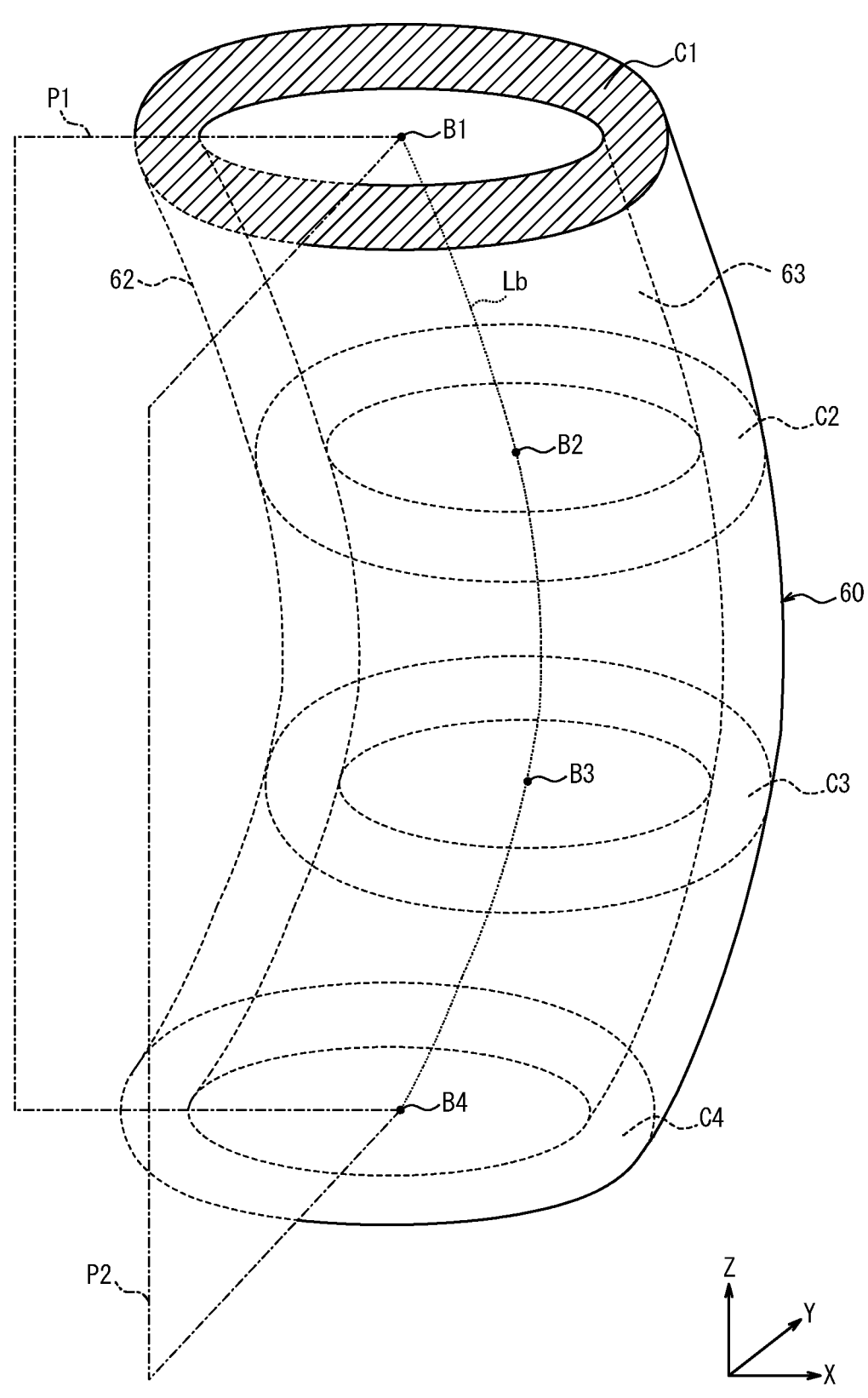
FIG. 4 is a diagram showing an example of a cutting region formed by the image processing system according to the embodiment of the present disclosure.

An image processing device 11 according to the present embodiment is a computer that causes a display 16 to display, as a three-dimensional image 53, three-dimensional data 52 representing a biological tissue 60. As shown in FIG. 4, the image processing device 11 forms, in the three-dimensional data 52, a cutting region 62 exposing a lumen 63 of the biological tissue 60 in the three-dimensional image 53. As shown in FIG. 2, the image processing device 11 causes the display 16 to display, together with the three-dimensional image 53, a two-dimensional image 56 representing a cross section 64 of the biological tissue 60 and a region 65 corresponding to the cutting region 62 in the cross section 64.

According to the present embodiment, it is possible to indicate how a part of a structure of the biological tissue 60 is cut out. Therefore, a user can understand based on the two-dimensional image 56 the kind of structure corresponding to a portion of the biological tissue 60 that has been cut out or omitted, and which is not displayed in the three-dimensional image 53. For example, if the user is an operator, it is rather easy to perform a treatment for the inside of the biological tissue 60.

The image processing device 11 generates and updates the three-dimensional data 52 based on tomographic data 51 of the biological tissue 60 acquired by a sensor that acquires the tomographic data 51 while moving through the lumen 63 of the biological tissue 60. As shown in FIG. 2, the image processing device 11 colors, in the three-dimensional image 53, at least a voxel representing an inner surface 61 of the biological tissue 60 or a voxel that is adjacent to the voxel representing the inner surface 61 and that represents the lumen 63 among a first voxel group 54 corresponding to the cross section 64 indicated by the tomographic data 51 newly acquired by the sensor, in a manner of being distinguished from a second voxel group 55 corresponding to another cross section of the biological tissue 60.

According to the present embodiment, it is possible to indicate which part in the three-dimensional image 53 the cross section 64 of the biological tissue 60 indicated by the tomographic data 51 newly acquired by the sensor corresponds to. Therefore, the user who observes the lumen 63 of the biological tissue 60 using the three-dimensional image 53 can rather easily understand which part in the three-dimensional image 53 information currently obtained by the sensor, that is, the latest information corresponds to.

In one modification of the present embodiment, the image processing device 11 may color not only the first voxel group 54 but also at least a voxel representing the inner surface 61 or a voxel that is adjacent to the voxel representing the inner surface 61 and that represents the lumen 63 among a voxel group corresponding to a cross section adjacent to the cross section 64 corresponding to the first voxel group 54, in a manner of being distinguished from a voxel group corresponding to another cross section of the biological tissue 60. According to the modification, a width of the voxel group that is colored in a manner of being distinguished from a voxel group corresponding to another cross section in a sensor moving direction is widened, and the user can rather easily recognize the voxel group in the three-dimensional image 53.

Figure 14:
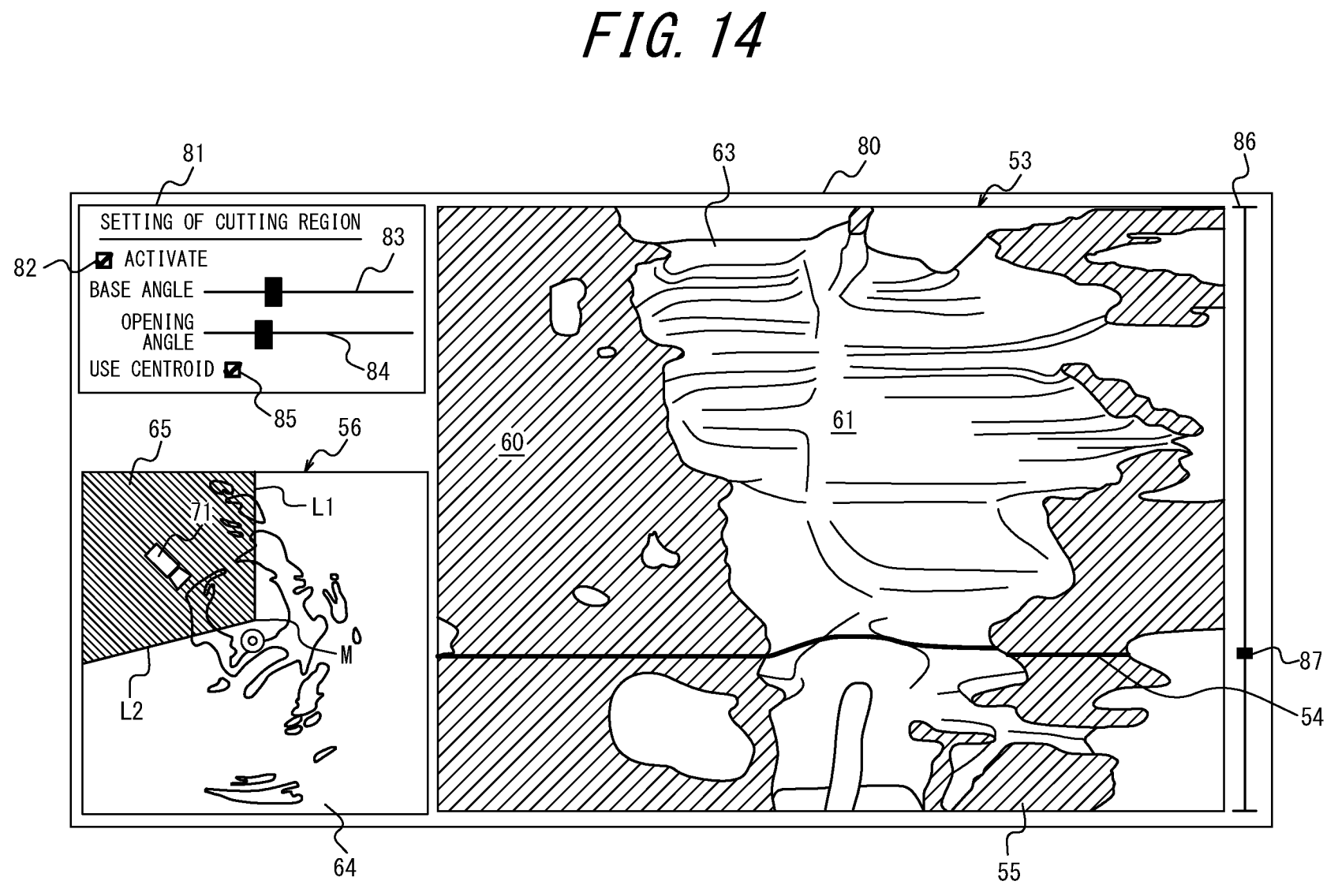

In one modification of the present embodiment, as shown in FIG. 14, all voxels representing the biological tissue 60 in the first voxel group 54 may be colored in a manner of being distinguished from the second voxel group 55. According to the modification, since the first voxel group 54 is colored in a manner of being distinguished from the second voxel group 55 on a cutting plane of the biological tissue 60 formed to observe the lumen 63 of the biological tissue 60, it is relatively easier for the user to understand which part in the three-dimensional image 53 the latest information corresponds to.

In the present embodiment, the image processing device 11 causes the display 16 to display the two-dimensional image 56 representing the cross section 64 together with the three-dimensional image 53 in which at least the voxel representing the inner surface 61 of the biological tissue 60 or the voxel that is adjacent to the voxel representing the inner surface 61 and that represents the lumen 63 among the first voxel group 54 corresponding to the cross section 64 is colored in a manner of being distinguished from the second voxel group 55 corresponding to the another cross section. Therefore, a relation between the two-dimensional image 56 and the three-dimensional image 53 can be shown.

The biological tissue 60 includes, for example, a blood vessel or an organ such as a heart. The biological tissue 60 is not limited to an anatomically single organ or a part of the anatomically single organ, and also includes a tissue having a lumen across a plurality of organs. Specific examples of such a tissue include a part of a vascular tissue from an upper portion of an inferior vena cava to a lower portion of a superior vena cava through a right atrium. In the example in FIGS. 2 to 4, the biological tissue 60 is a blood vessel.

In FIG. 2, an operation panel 81, the two-dimensional image 56, the three-dimensional image 53, a first graphic element 86, and a second graphic element 87 are displayed on a screen 80.

The operation panel 81 is a graphical user interface (GUI) component for setting the cutting region 62. The operation panel 81 can include a check box 82 for selecting whether to activate the setting of the cutting region 62, a slider 83 for setting a base angle, a slider 84 for setting an opening angle, and a check box 85 for selecting whether to use a centroid.

The base angle is a rotary angle of a straight line L1 of two straight lines L1 and L2 extending from one point M in a cross-sectional image representing the cross section 64 of the biological tissue 60. Therefore, setting the base angle corresponds to setting a direction of the straight line L1. The opening angle is an angle between the two straight lines L1 and L2. Therefore, setting the opening angle corresponds to setting an angle formed by the two straight lines L1 and L2. The point M is a centroid of the cross section 64. The point M may be set at a point other than the centroid on the cross section 64 when it is selected not to use the centroid.

The two-dimensional image 56 is an image obtained by processing a cross-sectional image. In the two-dimensional image 56, a color of the region 65 corresponding to the cutting region 62 is changed to clearly indicate which part of the cross section 64 is cut out (i.e., omitted) from the image 56.

In the present embodiment, a viewpoint when the three-dimensional image 53 is displayed on the screen 80 is adjusted according to a position of the cutting region 62. The term "viewpoint" refers to a position of a virtual camera 71 disposed in a three-dimensional space. In the two-dimensional image 56, a position of the camera 71 is shown with respect to the cross section 64.

In the present embodiment, the cutting region 62 can be determined using the two-dimensional image 56. Specifically, as shown in FIG. 3, by adjusting the base angle or the opening angle and setting a position or a size of the region 65 divided by the two straight lines L1 and L2 in the two-dimensional image 56, a position or a size of the cutting region 62 can be set. For example, when the base angle is changed such that the straight line L1 rotates counterclockwise by about 90 degrees, a region 65a after moving according to the change of the base angle is obtained in a two-dimensional image 56a. Then, the position of the cutting region 62 is adjusted according to a position of the region 65a. Alternatively, when the opening angle is changed such that the angle between the two straight lines L1 and L2 is increased, a region 65b after enlargement according to the change in the opening angle is obtained in a two-dimensional image 56b. Then, the size of the cutting region 62 is adjusted according to a size of the region 65b. By adjusting both the base angle and the opening angle and setting both the position and the size of the region 65 in the two-dimensional image 56, both the position and the size of the cutting region 62 can also be set. The position of the camera 71 may be appropriately adjusted according to the position or the size of the cutting region 62.

In the present embodiment, an image corresponding to a current position of the sensor, that is, the latest image is always displayed as the two-dimensional image 56, but in one modification of the present embodiment, an image corresponding to a position other than the current position of the sensor may be displayed as the two-dimensional image 56 after the cutting region 62 is determined.

In one modification of the present embodiment, the base angle may be set by dragging the straight line L1 or by inputting a numerical value, instead of setting by operating the slider 83. Similarly, the opening angle may be set by dragging the straight line L2 or by inputting a numerical value, instead of setting by operating the slider 84.

In the three-dimensional image 53, the cutting region 62 determined using the two-dimensional image 56 is hidden or transparent. In addition, in the three-dimensional image 53, the color of the first voxel group 54 corresponding to the current position of the sensor is changed in order to express a position in which the sensor is currently present in a longitudinal direction of the lumen 63 and which is currently updated in real time.

In the present embodiment, as shown in FIG. 2, the voxel representing the inner surface 61 of the biological tissue 60 among the first voxel group 54 is colored in a manner of being distinguished from the second voxel group 55 by setting the color to be different from that of the second voxel group 55, but in the modification of the present embodiment, as shown in FIG. 14, all voxels representing the biological tissue 60 among the first voxel group 54 may be set to a different color. In a further modification, instead of setting the first voxel group 54 and the second voxel group 55 to different colors, the first voxel group 54 may be colored in a manner of being distinguished from the second voxel group 55 by adjusting a contrast between the first voxel group 54 and the second voxel group 55.

The first graphic element 86 is a graphic element that represents a moving range of the sensor. The second graphic element 87 is a graphic element representing a position of the sensor. In the present embodiment, a combination of the first graphic element 86 and the second graphic element 87 is implemented as a slider. The first graphic element 86 and the second graphic element 87 may be displayed at any position, and are displayed on the right of the three-dimensional image 53 in the present embodiment.

In FIG. 4, an X-direction and a Y-direction orthogonal to the X-direction correspond to a lateral direction of the lumen 63 of the biological tissue 60. A Z-direction orthogonal to the X-direction and the Y-direction corresponds to the longitudinal direction of the lumen 63 of the biological tissue 60.

In an example in FIG. 4, the check box 85 on the operation panel 81 is in a checked state, that is, it is selected to use the centroid. The image processing device 11 calculates positions of centroids B1, B2, B3, and B4 of cross sections C1, C2, C3, and C4 of the biological tissue 60 using the three-dimensional data 52. The image processing device 11 sets, as cutting planes P1 and P2, two planes that intersect at a single line Lb passing through the positions of the centroids B1, B2, B3, and B4 and that include the respective two straight lines L1 and L2. For example, when the point M shown in FIG. 2 is the point B3, the straight line L1 is an intersection line between the cross section C3 and the cutting plane P1, and the straight line L2 is an intersection line between the cross section C3 and the cutting plane P2. The image processing device 11 forms, as the cutting region 62 in the three-dimensional data 52, a region interposed between the cutting planes P1 and P2 in the three-dimensional image 53 and exposing the lumen 63 of the biological tissue 60.

In the case of a three-dimensional model of the bent blood vessel as shown in FIG. 4, when the three-dimensional model is cut with one plane to display the lumen 63, there is a case in which the inside of the blood vessel cannot be correctly displayed. In the present embodiment, as shown in FIG. 4, by continuously capturing centroids of the blood vessel, the three-dimensional model can be cut such that the inside of the blood vessel can be reliably displayed.

In FIG. 4, for convenience, the four cross sections C1, C2, C3, and C4 are illustrated as a plurality of lateral cross sections of the lumen 63 of the biological tissue 60, but the number of cross sections serving as calculation targets of the centroid positions is not limited to four, and is preferably the same as the number of cross-sectional images acquired by IVUS.

In an example different from that in FIG. 4, the check box 85 on the operation panel 81 is in a not-checked state, that is, it is selected not to use the centroid. In such an example, the image processing device 11 sets, as the cutting planes P1 and P2, two planes that intersect at any single line passing through the point M, such as a straight line passing through the point M and extending in the Z-direction, and that include the respective two straight lines L1 and L2.

A configuration of an image processing system 10 according to the present embodiment will be described with reference to FIG. 1.

The image processing system 10 can include the image processing device 11, a cable 12, a drive unit 13, a keyboard 14, a mouse 15, and the display 16.

The image processing device 11 is a dedicated computer specialized for image diagnosis in the present embodiment, and may also be a general-purpose computer such as a personal computer (PC).

The cable 12 is used to connect the image processing device 11 and the drive unit 13.

Figure 5:
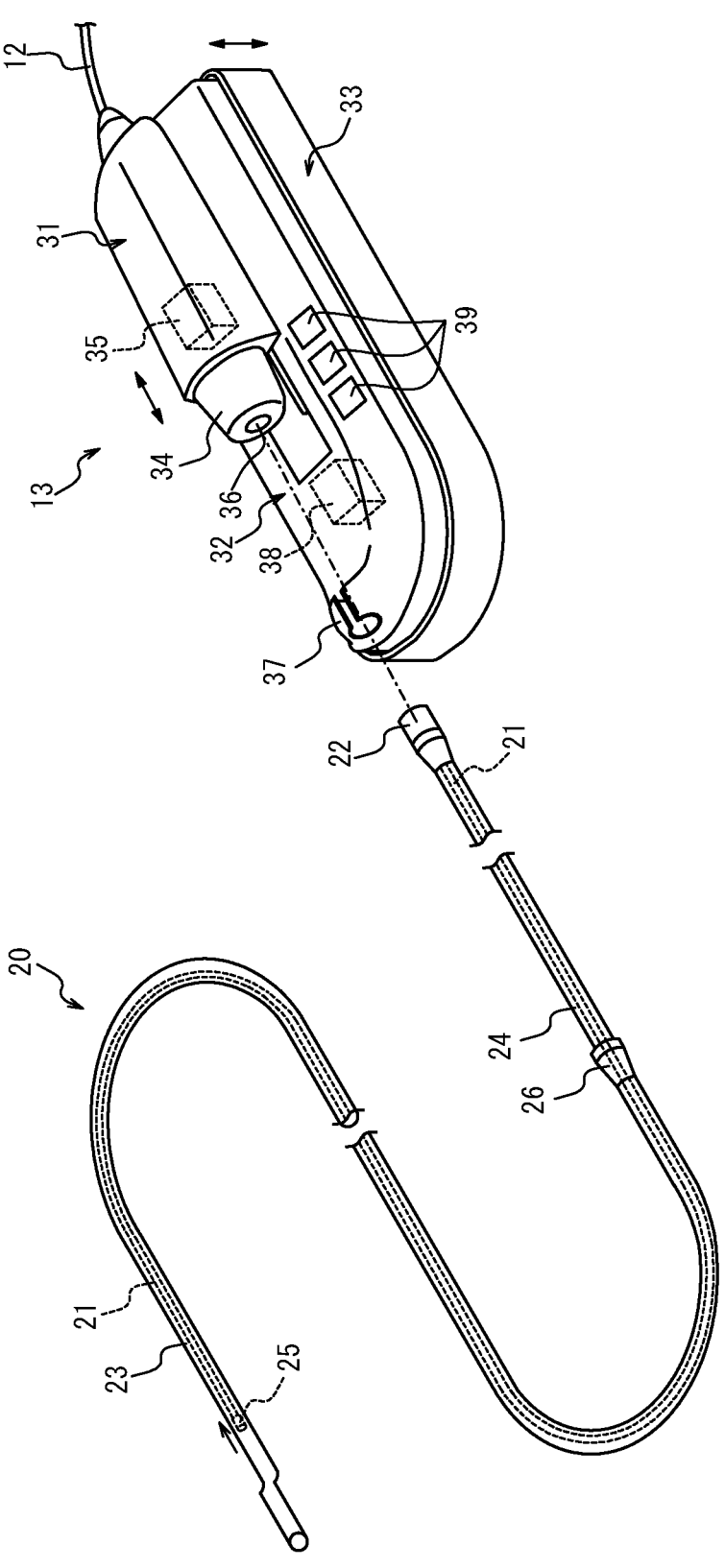
FIG. 5 is a perspective view of a probe and a drive unit according to the embodiment of the present disclosure.

The drive unit 13 is a device to be used by being connected to a probe 20 shown in FIG. 5 to drive the probe 20. The drive unit 13 is also referred to as a motor drive unit (MDU). The term "MDU" is an abbreviation for motor drive unit. The probe 20 is applied to IVUS. The probe 20 is also referred to as an IVUS catheter or an image diagnostic catheter.

The keyboard 14, the mouse 15, and the display 16 are connected to the image processing device 11 via a cable or wirelessly. The display 16 can be, for example, a liquid crystal display (LCD), an organic electro luminescence (EL) display, or a head-mounted display (HMD).

The image processing system 10 optionally further includes a connection terminal 17 and a cart unit 18.

The connection terminal 17 is used to connect the image processing device 11 and an external device. The connection terminal 17 can be, for example, a universal serial bus (USB) terminal. The external device can be, for example, a recording medium such as a magnetic disc drive, a magneto-optical disc drive, or an optical disc drive.

The cart unit 18 can be a cart equipped with casters for movement. The image processing device 11, the cable 12, and the drive unit 13 are disposed on a cart body of the cart unit 18. The keyboard 14, the mouse 15, and the display 16 are disposed on the uppermost table of the cart unit 18.

Configurations of the probe 20 and the drive unit 13 according to the present embodiment will be described with reference to FIG. 5.

The probe 20 can include a drive shaft 21, a hub 22, a sheath 23, an outer tube 24, an ultrasound transducer 25, and a relay connector 26.

The drive shaft 21 passes through the sheath 23 to be inserted into a lumen in a living body and the outer tube 24 connected to a proximal end of the sheath 23, and extends to an inside of the hub 22 provided at a proximal end of the probe 20. The drive shaft 21 is provided with the ultrasound transducer 25, which transmits and receives signals, at a distal end of the drive shaft 21, and is rotatably provided in the sheath 23 and the outer tube 24. The relay connector 26 connects the sheath 23 and the outer tube 24.

The hub 22, the drive shaft 21, and the ultrasound transducer 25 are connected to each other to integrally move forward and backward in an axial direction. Therefore, for example, when the hub 22 is pressed toward a distal side, the drive shaft 21 and the ultrasound transducer 25 move inside the sheath 23 toward the distal side. For example, when the hub 22 is pulled toward a proximal side, the drive shaft 21 and the ultrasound transducer 25 move inside the sheath 23 toward the proximal side as indicated by an arrow.

The drive unit 13 can include a scanner unit 31, a slide unit 32, and a bottom cover 33.

The scanner unit 31 is connected to the image processing device 11 via the cable 12. The scanner unit 31 can include a probe connection section 34 connected to the probe 20, and a scanner motor 35. The scanner motor 35 can be a drive source for rotating the drive shaft 21.

The probe connection section 34 is freely detachably connected to the probe 20 through an insertion port 36 of the hub 22 provided at the proximal end of the probe 20. Inside the hub 22, a proximal end of the drive shaft 21 is rotatably supported, and a rotational force of the scanner motor 35 is transmitted to the drive shaft 21. A signal is transmitted and received between the drive shaft 21 and the image processing device 11 via the cable 12. In the image processing device 11, generation of a tomographic image of a body lumen and image processing are executed based on the signal transmitted from the drive shaft 21.

The slide unit 32 is mounted with the scanner unit 31 in a manner of being capable of moving forward and backward, and is mechanically and electrically connected to the scanner unit 31. The slide unit 32 can include a probe clamp section 37, a slide motor 38, and a switch group 39.

The probe clamp section 37 is disposed coaxially with the probe connection section 34 on a distal side relative to the probe connection section 34, and supports the probe 20 to be connected to the probe connection section 34.

The slide motor 38 is a drive source that generates a drive force in the axial direction. The scanner unit 31 moves forward and backward when driven by the slide motor 38, and the drive shaft 21 moves forward and backward in the axial direction accordingly. The slide motor 38 can be, for example, a servo motor.

The switch group 39 can include, for example, a forward switch and a pull-back switch that are pressed when the scanner unit 31 is to be moved forward or backward, and a scan switch that is pressed when image drawing is to be started or ended. Various switches may be included in the switch group 39 as necessary without being limited to the example here.

When the forward switch is pressed, the slide motor 38 rotates forward, and the scanner unit 31 moves forward. Meanwhile, when the pull-back switch is pressed, the slide motor 38 rotates backward, and the scanner unit 31 moves backward.

When the scan switch is pressed, the image drawing is started, the scanner motor 35 is driven, and the slide motor 38 is driven to move the scanner unit 31 backward. The user such as the operator connects the probe 20 to the scanner unit 31 in advance, and the drive shaft 21 rotates and moves toward the proximal side in the axial direction upon the start of the image drawing. When the scan switch is pressed again, the scanner motor 35 and the slide motor 38 are stopped, and the image drawing is ended.

The bottom cover 33 covers a bottom and an entire circumference of a side surface on a bottom side of the slide unit 32, and is capable of moving toward and away from the bottom of the slide unit 32.

Figure 6:
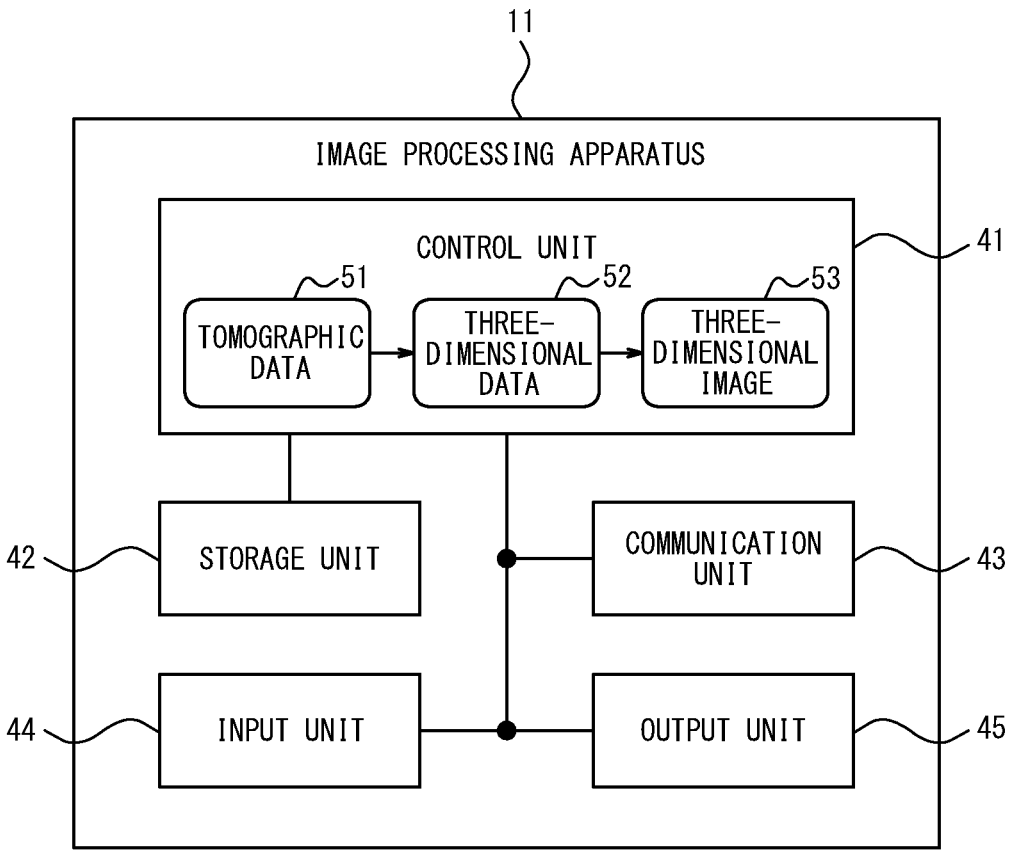
FIG. 6 is a block diagram showing a configuration of an image processing device according to the embodiment of the present disclosure.

A configuration of the image processing device 11 will be described with reference to FIG. 6.

The image processing device 11 includes a control unit 41, a storage unit 42, a communication unit 43, an input unit 44, and an output unit 45.

The control unit 41 includes at least one processor, at least one programmable circuit, at least one dedicated circuit, or any combination of the at least one processor, the at least one programmable circuit, and the at least one dedicated circuit. The processor is a general-purpose processor such as a central processing unit (CPU) or a graphics processing unit (GPU), or a dedicated processor specialized for specific processing. The programmable circuit can be, for example, a field-programmable gate array (FPGA). The dedicated circuit can be, for example, an application specific integrated circuit (ASIC). The control unit 41 executes processing related to an operation of the image processing device 11 while controlling each unit of the image processing system 10 including the image processing device 11.

The storage unit 42 includes at least one semiconductor memory, at least one magnetic memory, at least one optical memory, or any combination of the at least one semiconductor memory, the at least one magnetic memory, and the at least one optical memory. The semiconductor memory can be, for example, a random access memory (RAM) or a read only memory (ROM). The RAM can be, for example, a static random access memory (SRAM) or a dynamic random access memory (DRAM). The ROM can be, for example, an electrically erasable programmable read only memory (EE-PROM). The storage unit 42 functions as, for example, a main storage device, an auxiliary storage device, or a cache memory. The storage unit 42 stores data used for the operation of the image processing device 11, such as the tomographic data 51, and data obtained by the operation of the image processing device 11, such as the three-dimensional data 52 and the three-dimensional image 53.

The communication unit 43 includes at least one communication interface. The communication interface is, for example, a wired local area network (LAN) interface, a wireless LAN interface, or an image diagnostic interface for receiving IVUS signals and performing analog to digital (A/D) conversion for the IVUS signals. The communication unit 43 receives the data used for the operation of the image processing device 11 and transmits the data obtained by the operation of the image processing device 11. In the present embodiment, the drive unit 13 is connected to the image diagnostic interface included in the communication unit 43.

The input unit 44 includes at least one input interface. The input interface can be, for example, a USB interface, a High-Definition Multimedia Interface (HDMI®) interface, or an interface compatible with a short-range wireless communication standard such as Bluetooth®. The input unit 44 receives an operation by the user such as an operation of inputting data used for the operation of the image processing device 11. In the present embodiment, the keyboard 14 and the mouse 15 are connected to the USB interface or the interface compatible with a short-range wireless communication standard included in the input unit 44. When a touch screen is provided integrally with the display 16, the display 16 may be connected to the USB interface or the HDMI interface included in the input unit 44.

The output unit 45 includes at least one output interface. The output interface can be, for example, a USB interface, an HDMI interface, or an interface compatible with a short-range wireless communication standard such as Bluetooth. The output unit 45 outputs the data obtained by the operation of the image processing device 11. In the present embodiment, the display 16 is connected to the USB interface or the HDMI interface included in the output unit 45.

A function of the image processing device 11 is implemented by executing an image processing program according to the present embodiment by a processor as the control unit 41. That is, the function of the image processing device 11 is implemented by software. The image processing program causes a computer to function as the image processing device 11 by causing the computer to execute the operation of the image processing device 11. That is, the computer functions as the image processing device 11 by executing the operation of the image processing device 11 according to the image processing program.

The program may be stored in a non-transitory computer-readable medium in advance. The non-transitory computer-readable medium can be, for example, a flash memory, a magnetic recording device, an optical disc, a magneto-optical recording medium, or a ROM. Distribution of the program is executed by, for example, selling, transferring, or lending a portable medium such as a secure digital (SD) card, a digital versatile disc (DVD) or a compact disc read only memory (CD-ROM) storing the program. The program may be distributed by storing the program in a storage of a server in advance and transferring the program from the server to another computer. The program may be provided as a program product.

For example, the computer temporarily stores, in the main storage device, the program stored in the portable medium or the program transferred from the server. The computer reads, by the processor, the program stored in the main storage device, and executes, by the processor, processing according to the read program. The computer may read the program directly from the portable medium and execute the processing according to the program. Each time the program is transferred from the server to the computer, the computer may sequentially execute processing according to the received program. The processing may be executed by a so-called application service provider (ASP) type service in which the function is implemented only by execution instruction and result acquisition without transferring the program from the server to the computer. The program includes information provided for processing by an electronic computer and conforming to the program. For example, data that is not a direct command to the computer but has a property of defining the processing of the computer corresponds to the "information conforming to the program".

The functions of the image processing device 11 may be partially or entirely implemented by the programmable circuit or the dedicated circuit as the control unit 41. That is, the functions of the image processing device 11 may be partially or entirely implemented by hardware.

An operation of the image processing system 10 according to the present embodiment will be described with reference to FIGS. 7 and 8. The operation of the image processing system 10 corresponds to an image display method according to the present embodiment.

Figure 7:
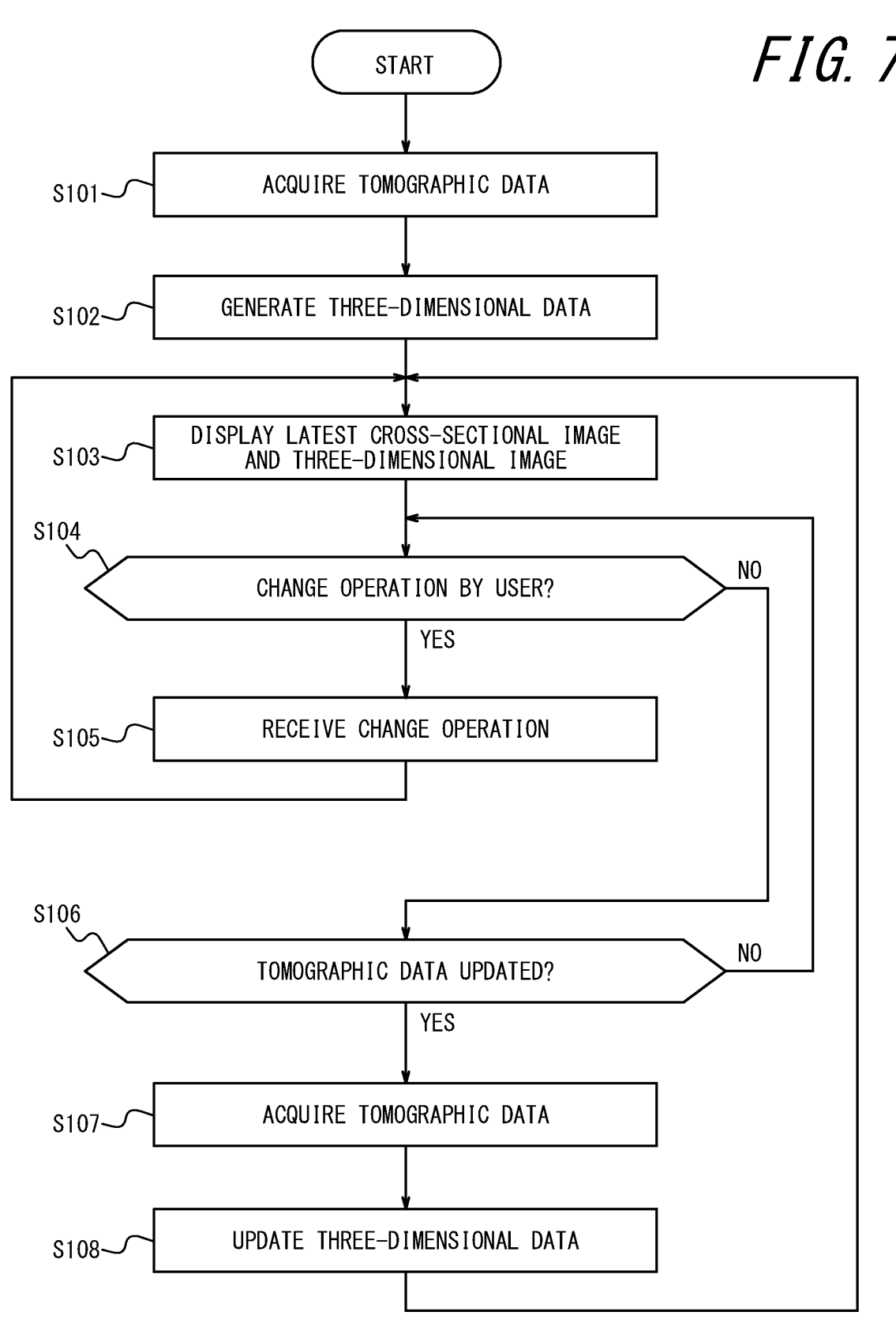
FIG. 7 is a flowchart illustrating an operation of the image processing system according to the embodiment of the present disclosure.

Before a start of a flow in FIG. 7, the probe 20 is primed by the user. Thereafter, the probe 20 is fitted into the probe connection section 34 and the probe clamp section 37 of the drive unit 13, and is connected and fixed to the drive unit 13. Then, the probe 20 is inserted to a target site in the biological tissue 60 such as a blood vessel or a heart.

In S101, the scan switch included in the switch group 39 is pressed, and a so-called pull-back operation is executed by pressing the pull-back switch included in the switch group 39. The probe 20 transmits an ultrasound inside the biological tissue 60 by the ultrasound transducer 25 that moves backward in the axial direction by the pull-back operation. The ultrasound transducer 25 radially transmits the ultrasound while moving inside the biological tissue 60. The ultrasound transducer 25 receives a reflected wave of the transmitted ultrasound. The probe 20 inputs a signal of the reflected wave received by the ultrasound transducer 25 to the image processing device 11. The control unit 41 of the image processing device 11 processes the input signal to sequentially generate cross-sectional images of the biological tissue 60, thereby acquiring the tomographic data 51, which includes a plurality of cross-sectional images.

Specifically, the probe 20 transmits, by the ultrasound transducer 25, the ultrasound in a plurality of directions from a rotation center to an outside while causing the ultrasound transducer 25 to rotate in a circumferential direction and to move in the axial direction inside the biological tissue 60. The probe 20 receives, by the ultrasound transducer 25, the reflected wave from a reflecting object present in each of the plurality of directions inside the biological tissue 60. The probe 20 transmits the signal of the received reflected wave to the image processing device 11 via the drive unit 13 and the cable 12. The communication unit 43 of the image processing device 11 receives the signal transmitted from the probe 20. The communication unit 43 performs A/D conversion for the received signal. The communication unit 43 inputs the signal after A/D conversion to the control unit 41. The control unit 41 processes the input signal to calculate an intensity value distribution of the reflected wave from the reflecting object present in a transmission direction of the ultrasound of the ultrasound transducer 25. The control unit 41 sequentially generates two-dimensional images having a luminance value distribution corresponding to the calculated intensity value distribution as the cross-sectional images of the biological tissue 60, thereby acquiring the tomographic data 51 which is a data set of the cross-sectional images. The control unit 41 stores the acquired tomographic data 51 in the storage unit 42.

In the present embodiment, the signal of the reflected wave received by the ultrasound transducer 25 corresponds to raw data of the tomographic data 51, and the cross-sectional images generated by processing the signal of the reflected wave with the image processing device 11 correspond to processed data of the tomographic data 51.

In one modification of the present embodiment, the control unit 41 of the image processing device 11 may store the signal input from the probe 20 as it is in the storage unit 42 as the tomographic data 51. Alternatively, the control unit 41 may store data indicating the intensity value distribution of the reflected wave calculated by processing the signal input from the probe 20 in the storage unit 42 as the tomographic data 51. That is, the tomographic data 51 is not limited to the data set of the cross-sectional images of the biological tissue 60, and may be data representing a cross section of the biological tissue 60 at each moving position of the ultrasound transducer 25 in any format.

In one modification of the present embodiment, an ultrasound transducer that transmits the ultrasound in the plurality of directions without rotation may be used instead of the ultrasound transducer 25 that transmits the ultrasound in the plurality of directions while rotating in the circumferential direction.

In one modification of the present embodiment, the tomographic data 51 may be acquired by using optical frequency domain imaging (OFDI) or optical coherence tomography (OCT) instead of being acquired by using IVUS. The term "OFDI" is an abbreviation for optical frequency domain imaging. When OFDI or OCT is used, as a sensor that acquires the tomographic data 51 while moving in the lumen 63 of the biological tissue 60, a sensor that acquires the tomographic data 51 by emitting light in the lumen 63 of the biological tissue 60 is used instead of the ultrasound transducer 25 that acquires the tomographic data 51 by transmitting the ultrasound in the lumen 63 of the biological tissue 60.

In one modification of the present embodiment, instead of the image processing device 11 generating the data set of the cross-sectional images of the biological tissue 60, another device may generate the same data set, and the image processing device 11 may acquire the data set from the another device. That is, instead of the control unit 41 of the image processing device 11 processing the IVUS signal to generate the cross-sectional images of the biological tissue 60, another device may process the IVUS signal to generate the cross-sectional images of the biological tissue 60 and input the generated cross-sectional images to the image processing device 11.

In S102, the control unit 41 of the image processing device 11 generates the three-dimensional data 52 of the biological tissue 60 based on the tomographic data 51 acquired in S101. That is, the control unit 41 generates the three-dimensional data 52 based on the tomographic data 51 acquired by the sensor. Here, when the already generated three-dimensional data 52 is present, it is preferable to update only data at a location corresponding to the updated tomographic data 51, instead of regenerating all the three-dimensional data 52 from the beginning. In this case, a data processing amount when generating the three-dimensional data 52 can be reduced, and a real-time property of the three-dimensional image 53 in S103 can be improved, and wherein S103 is subsequent or after S102.

Specifically, the control unit 41 of the image processing device 11 generates the three-dimensional data 52 of the biological tissue 60 by stacking the cross-sectional images of the biological tissue 60 included in the tomographic data 51 stored in the storage unit 42, and converting the same into three-dimensional data. As a method for three-dimensional conversion, any method among a rendering method such as surface rendering or volume rendering, and various types of processing such as texture mapping including environment mapping, and bump mapping, which are associated with the rendering method, can be used. The control unit 41 stores the generated three-dimensional data 52 in the storage unit 42.

In S103, the control unit 41 of the image processing device 11 causes the display 16 to display the three-dimensional data 52 generated in S102 as the three-dimensional image 53. At this time, the control unit 41 may set an angle for displaying the three-dimensional image 53 to any angle. The control unit 41 causes the display 16 to display the latest cross-sectional image included in the tomographic data 51 acquired in S101 together with the three-dimensional image 53.

Specifically, the control unit 41 of the image processing device 11 generates the three-dimensional image 53 based on the three-dimensional data 52 stored in the storage unit 42. The control unit 41 causes the display 16 to display, via the output unit 45, the generated three-dimensional image 53, and the latest cross-sectional image among the cross-sectional images of the biological tissue 60 included in the tomographic data 51 stored in the storage unit 42.

In the present embodiment, the control unit 41 of the image processing device 11 colors, in the three-dimensional image 53, the voxel representing the inner surface 61 of the biological tissue 60 among the first voxel group 54 corresponding to the cross section 64 indicated by the tomographic data 51 newly acquired by the sensor, in a manner of being distinguished from the second voxel group 55 corresponding to the another cross section of the biological tissue 60. Specifically, as shown in FIG. 2, the control unit 41 sets the voxel representing the inner surface 61 of the biological tissue 60 among the first voxel group 54 to a color different from any color of the second voxel group 55, thereby coloring the voxel representing the inner surface 61 of the biological tissue 60 among the first voxel group 54 in a manner of being distinguished from the second voxel group 55.

In one modification of the present embodiment, as shown in FIG. 14, the control unit 41 of the image processing device 11 may color all of the voxels representing the biological tissue 60 among the first voxel group 54 in a manner of being distinguished from the second voxel group 55. Specifically, the control unit 41 may set all of the voxels representing the biological tissue 60 among the first voxel group 54 to a color different from any color of the second voxel group 55, thereby coloring all of the voxels representing the biological tissue 60 among the first voxel group 54 in a manner of being distinguished from the second voxel group 55.

In the present embodiment, the control unit 41 of the image processing device 11 combines the first graphic element 86 and the second graphic element 87 and causes the display 16 to display the same together with the three-dimensional image 53. Specifically, as shown in FIG. 2, the control unit 41 causes the slider implemented by combining the first graphic element 86 and the second graphic element 87 to be displayed on the right of the three-dimensional image 53 via the output unit 45.

In the present embodiment, the control unit 41 of the image processing device 11 causes the display 16 to display the first graphic element 86 in a direction in which the longitudinal direction of the lumen 63 in the three-dimensional image 53 and a long axis direction of the first graphic element 86 are parallel to each other. Specifically, as shown in FIG. 2, the control unit 41 matches the moving range of the sensor indicated by the first graphic element 86 with a display range of the three-dimensional image 53 in a vertical direction of the screen 80, and matches the position of the sensor indicated by the second graphic element 87 with a position of the first voxel group 54.

In S104, if there is an operation of setting the angle for displaying the three-dimensional image 53 as a change operation by the user, processing in S105 is executed. If there is no change operation by the user, processing in S106 is executed.

In S105, the control unit 41 of the image processing device 11 receives, via the input unit 44, the operation of setting the angle for displaying the three-dimensional image 53. The control unit 41 adjusts the angle for displaying the three-dimensional image 53 to the set angle. Then, in S103, the control unit 41 causes the display 16 to display the three-dimensional image 53 at the angle set in S105.

Specifically, the control unit 41 of the image processing device 11 receives, via the input unit 44, an operation by the user of rotating the three-dimensional image 53 displayed on the display 16 by using the keyboard 14, the mouse 15, or the touch screen provided integrally with the display 16. The control unit 41 interactively adjusts the angle for displaying the three-dimensional image 53 on the display 16 according to the operation by the user. Alternatively, the control unit 41 receives, via the input unit 44, an operation by the user of inputting a numerical value of the angle for displaying the three-dimensional image 53 by using the keyboard 14, the mouse 15, or the touch screen provided integrally with the display 16. The control unit 41 adjusts the angle for displaying the three-dimensional image 53 on the display 16 in accordance with the input numerical value.

In S106, if the tomographic data 51 is updated, processing in S107 and S108 is executed. If the tomographic data 51 is not updated, the presence or absence of the change operation by the user is confirmed again in S104.

In S107, similar to the processing in S101, the control unit 41 of the image processing device 11 processes the signal input from the probe 20 to newly generate cross-sectional images of the biological tissue 60, thereby acquiring the tomographic data 51 including at least one new cross-sectional image.

In S108, the control unit 41 of the image processing device 11 updates the three-dimensional data 52 of the biological tissue 60 based on the tomographic data 51 acquired in S107. That is, the control unit 41 updates the three-dimensional data 52 based on the tomographic data 51 acquired by the sensor. Then, in S103, the control unit 41 causes the display 16 to display the three-dimensional data 52 updated in S108 as the three-dimensional image 53. The control unit 41 causes the display 16 to display the latest cross-sectional image included in the tomographic data 51 acquired in S107 together with the three-dimensional image 53. In S108, it is preferable to update only data at a location corresponding to the updated tomographic data 51. In this case, the data processing amount when generating the three-dimensional data 52 can be reduced, and the real-time property of the three-dimensional image 53 can be improved in S108.

In S111, if there is an operation of setting the cutting region 62 as a setting operation by the user, processing in S112 is executed.

In S112, the control unit 41 of the image processing device 11 receives, via the input unit 44, the operation of setting the cutting region 62.

Specifically, the control unit 41 of the image processing device 11 receives, via the input unit 44, an operation of setting the region 65 corresponding to the cutting region 62 on the cross-sectional image displayed on the display 16 in S103. In the present embodiment, the control unit 41 receives an operation of setting the two straight lines L1 and L2 extending from the point M in the cross-sectional image as the operation of setting the region 65 corresponding to the cutting region 62.

More specifically, the control unit 41 of the image processing device 11 receives, via the input unit 44, an operation by the user of designating the base angle and the opening angle by using the keyboard 14, the mouse 15, or the touch screen provided integrally with the display 16 on the operation panel 81 as shown in FIG. 2. That is, the control unit 41 receives an operation of designating the direction of the straight line L1 of the two straight lines L1 and L2 and the angle formed by the two straight lines L1 and L2 as the operation of setting the two straight lines L1 and L2. Here, the check box 85 on the operation panel 81 is in a checked state, that is, it is selected to use the centroid.

In one modification of the present embodiment, the control unit 41 of the image processing device 11 may receive, via the input unit 44, an operation by the user of drawing the two straight lines L1 and L2 by using the keyboard 14, the mouse 15, or the touch screen provided integrally with the display 16 on the cross-sectional image displayed on the display 16. That is, the control unit 41 may receive the operation of drawing the two straight lines L1 and L2 on the cross-sectional image as the operation of setting the two straight lines L1 and L2.

In S113, the control unit 41 of the image processing device 11 calculates centroid positions of a plurality of lateral cross sections of the lumen 63 of the biological tissue 60 by using the latest three-dimensional data 52 stored in the storage unit 42. The latest three-dimensional data 52 is the three-dimensional data 52 generated in S102 if the processing in S108 is not executed, and is the three-dimensional data 52 updated in S108 if the processing in S108 is executed. Here, when the already generated three-dimensional data 52 is present, it is preferable to update only data at a location corresponding to the updated tomographic data 51, instead of regenerating all the three-dimensional data 52 from the beginning. In this case, the data processing amount when generating the three-dimensional data 52 can be reduced, and the real-time property of the three-dimensional image 53 in a subsequent S117 can be improved.

Figure 9:
FIG. 9 is a diagram showing a result of binarizing a cross-sectional image of a biological tissue in the embodiment of the present disclosure.
Figure 10:
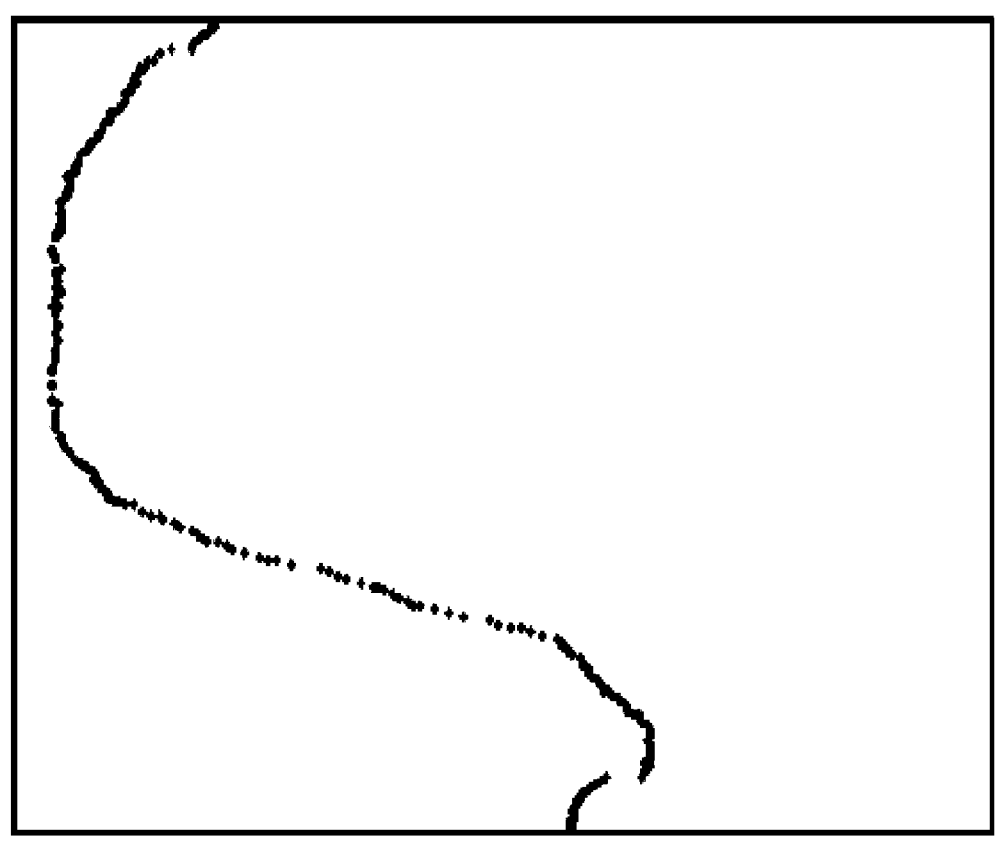
FIG. 10 is a diagram showing a result of extracting a point group on an inner surface of the biological tissue in the embodiment of the present disclosure.

Specifically, as shown in FIG. 9, if the control unit 41 of the image processing device 11 generates a corresponding new cross-sectional image in S107 for each of the plurality of cross-sectional images generated in S101, the control unit 41 replaces each of the plurality of cross-sectional images generated in S101 with the new cross-sectional image, and then binarizes the cross-sectional image. As shown in FIG. 10, the control unit 41 extracts a point group on an inner surface of the biological tissue 60 from the binarized cross-sectional image. For example, the control unit 41 extracts a point group on an inner surface of a blood vessel by extracting, one by one, points corresponding to an inner surface of a main blood vessel along a vertical direction of the cross-sectional image having an r-axis as a horizontal axis and a 0-axis as a vertical axis. The control unit 41 may simply obtain a centroid of the extracted point group on the inner surface, but in this case, since the point group is not uniformly sampled over the inner surface, a centroid position shifts. Therefore, in the present embodiment, the control unit 41 calculates a convex hull of the extracted point group on the inner surface, and calculates a centroid position $C_n=(C_x, C_y)$ by using a formula for obtaining a centroid of a polygon as follows. In the following formula, n vertices $(x_0, y_0)$, $(x_1, y_1)$, . . . , $(x_{n-1}, y_{n-1})$ are regarded as being present on the convex hull counterclockwise as the point group on the inner surface as shown in FIG. 10, and $(x_n, y_n)$ is regarded as $(x_0, y_0)$.

$$C_x = \frac{1}{6A}\sum_{i=0}^{n-1}(x_i + x_{i+1})(x_i y_{i+1} - x_{i+1} y_i) \qquad \text{Formula 1}$$

$$C_y = \frac{1}{6A}\sum_{i=0}^{n-1}(y_i + y_{i+1})(x_i y_{i+1} - x_{i+1} y_i)$$

$$A = \frac{1}{2}\sum_{i=0}^{n-1}(x_i y_{i+1} - x_{i+1} y_i)$$

Figure 11:
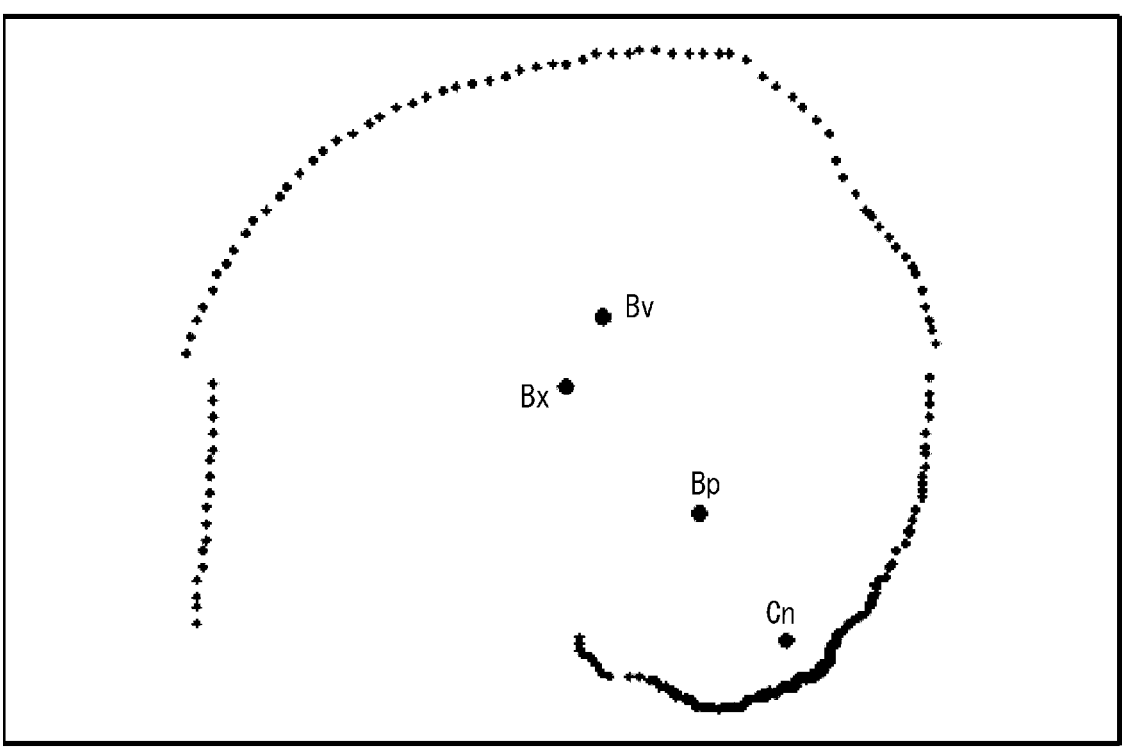
FIG. 11 is a diagram showing a result of calculating a centroid position of a cross section of the biological tissue in the embodiment of the present disclosure.

The centroid positions obtained as results are shown in FIG. 11. In FIG. 11, a point Cn is a center of the cross-sectional image. A point Bp is a centroid of the point group on the inner surface. A point Bv is a centroid of vertices of the polygon. A point Bx is a centroid of the polygon serving as the convex hull.

As a method of calculating the centroid position of the blood vessel, a method other than the method of calculating the centroid position of the polygon serving as the convex hull may be used. For example, with respect to an original cross-sectional image that is not binarized, a method of calculating a center position of a maximum circle that falls within the main blood vessel as the centroid position may be used. Alternatively, with respect to the binarized cross-sectional image having the r-axis as the horizontal axis and the e-axis as the vertical axis, a method of calculating an average position of pixels in a main blood vessel region as the centroid position may be used. The same method as described above may also be used when the biological tissue 60 is not a blood vessel.

In S114, the control unit 41 of the image processing device 11 smooths calculation results of the centroid positions in S113.

Figure 12:
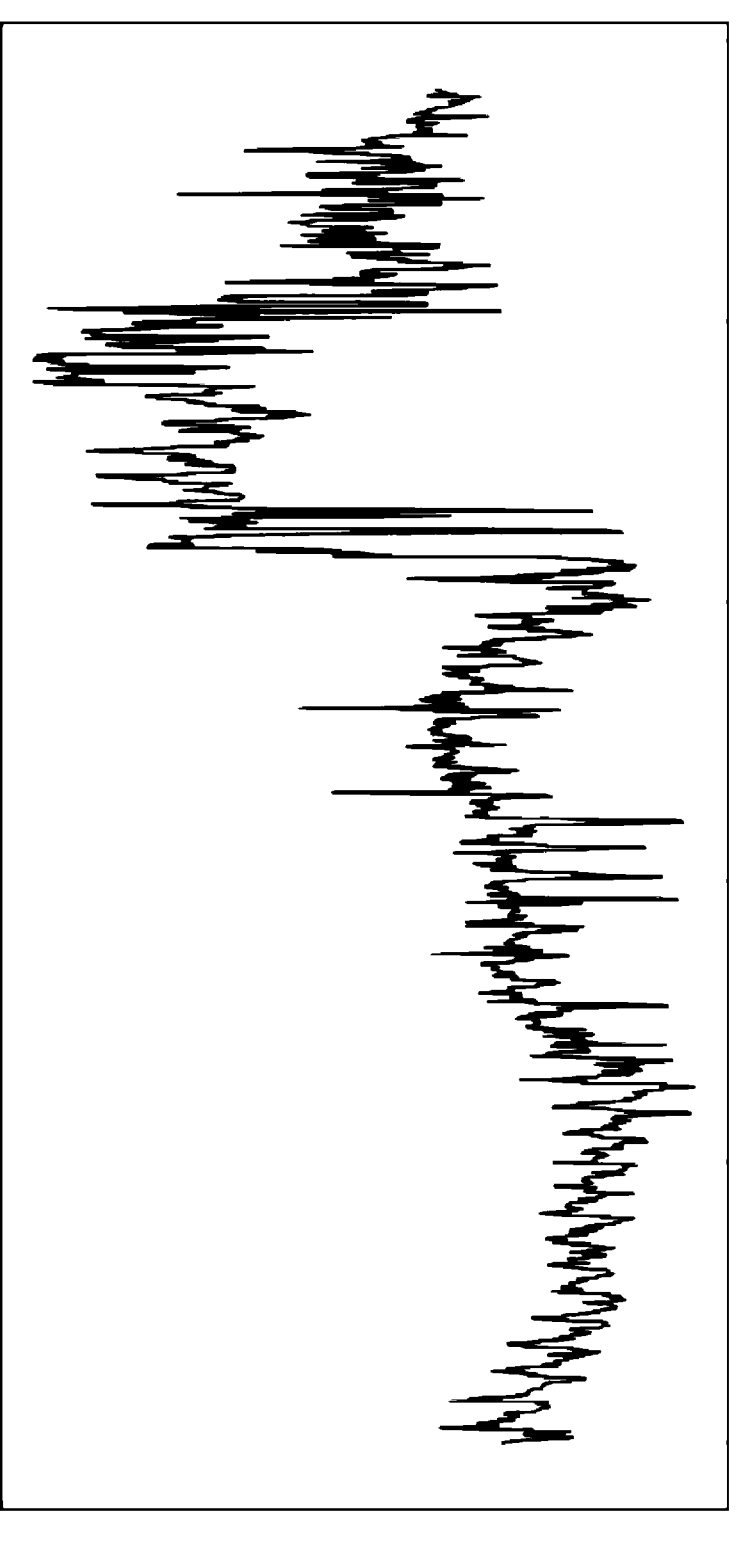
FIG. 12 is a diagram showing results of calculating centroid positions of a plurality of cross sections of the biological tissue in the embodiment of the present disclosure.
Figure 13:
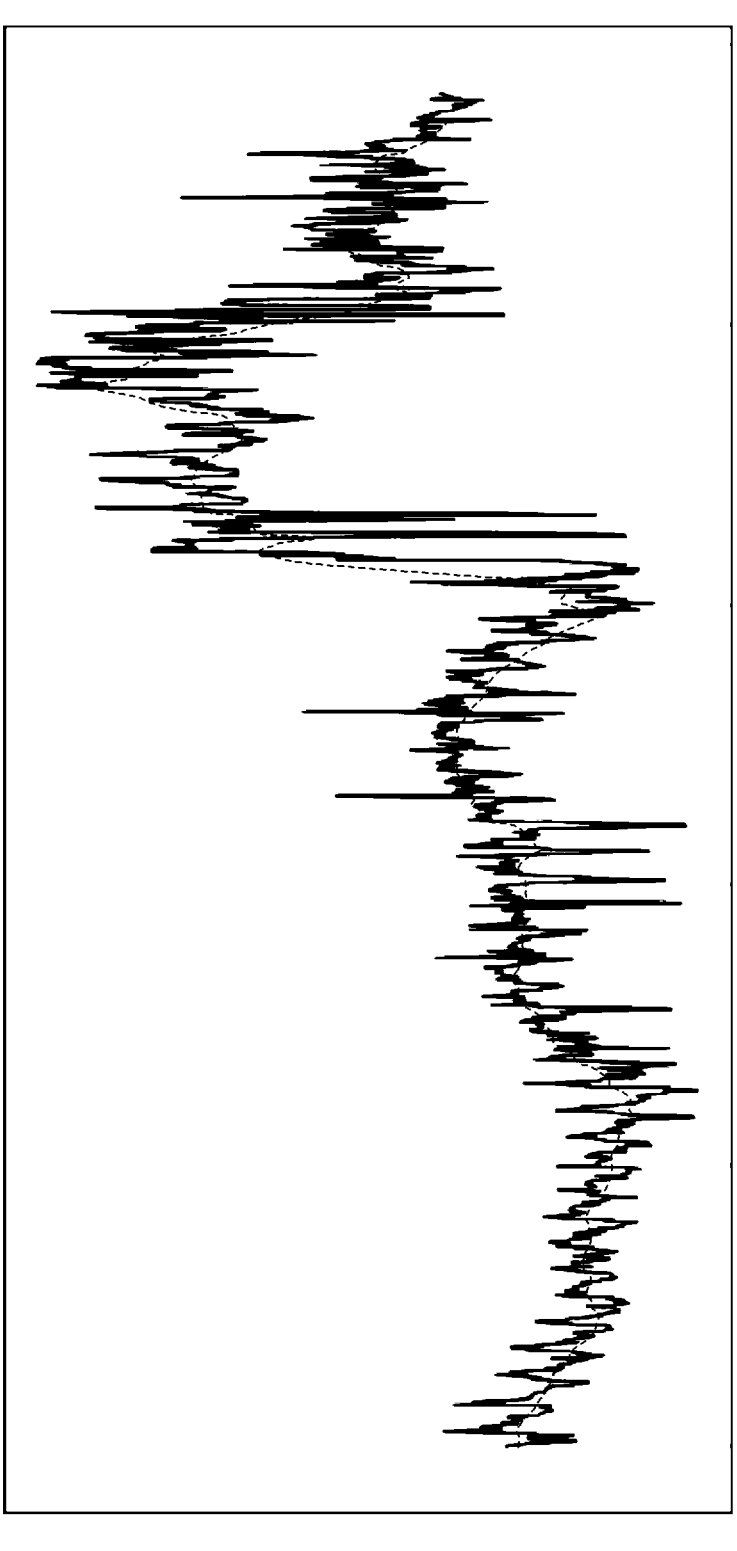
FIG. 13 is a diagram showing a result of smoothing the results in FIG. 12.

As shown in FIG. 12, when the calculation results of the centroid positions are viewed as a time function, it can be seen that an influence of pulsation is large. Therefore, in the present embodiment, the control unit 41 of the image processing device 11 smooths the calculation results of the centroid positions by using moving average as indicated by a broken line in FIG. 13.

As a smoothing method, a method other than moving average may be used. For example, an exponential smoothing method, a kernel method, local regression, a Ramer-Douglas-Peucker algorithm, a Savitzky-Golay method, smoothing spline, or stretched grid method (SGM) may be used. Alternatively, a method of executing a fast Fourier transform and then removing a high frequency component may be used. Alternatively, a Kalman filter or a low-pass filter such as a Butterworth filter, a Chebyshev filter, a digital filter, an elliptic filter, or a Kolmogorov-Zurbenko (KZ) filter may be used.

When smoothing is simply executed, the centroid positions may enter the tissue. In this case, the control unit 41 may divide the calculation results of the centroid positions according to positions of a plurality of lateral cross sections of the lumen 63 of the biological tissue 60 in the longitudinal direction of the lumen 63 of the biological tissue 60, and may smooth each of the divided calculation results. That is, when a curve of the centroid positions as indicated by the broken line in FIG. 13 overlaps a tissue region, the control unit 41 may divide the curve of the centroid positions into a plurality of sections and smooth each section. Alternatively, the control unit 41 may adjust a degree of smoothing to be executed on the calculation results of the centroid positions according to the positions of the plurality of lateral cross sections of the lumen 63 of the biological tissue 60 in the longitudinal direction of the lumen 63 of the biological tissue 60. That is, when the curve of the centroid positions as indicated by the broken line in FIG. 13 overlaps the tissue region, the control unit 41 may decrease the degree of smoothing to be executed on a part of a section including overlapping points.

In S115, as shown in FIG. 4, the control unit 41 of the image processing device 11 sets, as the cutting planes P1 and P2, two planes intersecting at the single line Lb passing through the centroid positions calculated in S113. In the present embodiment, the control unit 41 smooths the calculation results of the centroid positions in S114 and then sets the cutting planes P1 and P2, but the processing in S114 may be omitted.

Specifically, the control unit 41 of the image processing device 11 sets, as the line Lb, a curve of the centroid positions obtained as a result of the smoothing in S114. The control unit 41 sets, as the cutting planes P1 and P2, the two planes that intersect at the set line Lb and that include the respective two straight lines L1 and L2 set in S112. The control unit 41 specifies three-dimensional coordinates intersecting with the cutting planes P1 and P2 of the biological tissue 60 in the latest three-dimensional data 52 stored in the storage unit 42 as three-dimensional coordinates of an edge of an opening exposing the lumen 63 of the biological tissue 60 in the three-dimensional image 53. The control unit 41 stores the specified three-dimensional coordinates in the storage unit 42.

In S116, the control unit 41 of the image processing device 11 forms, as the cutting region 62 in the three-dimensional data 52, the region interposed between the cutting planes P1 and P2 in the three-dimensional image 53 and exposing the lumen 63 of the biological tissue 60.

Specifically, the control unit 41 of the image processing device 11 sets a portion in the latest three-dimensional data 52 stored in the storage unit 42 that is specified by the three-dimensional coordinates stored in the storage unit 42 to be hidden or transparent when the three-dimensional image 53 is to be displayed on the display 16. That is, the control unit 41 forms the cutting region 62 in accordance with the region 65 set in S112.

In S117, the control unit 41 of the image processing device 11 causes the display 16 to display the three-dimensional data 52 having the cutting region 62 formed in S116 as the three-dimensional image 53. The control unit 41 causes the display 16 to display, together with the three-dimensional image 53, the two-dimensional image 56 representing the cross section 64 indicated by the tomographic data 51 newly acquired by the sensor and the region 65 corresponding to the cutting region 62 in the cross section 64, which are represented by the cross-sectional image displayed on the display 16 in S103.

Specifically, the control unit 41 of the image processing device 11 processes the latest cross-sectional image among the cross-sectional images of the biological tissue 60 included in the tomographic data 51 stored in the storage unit 42 to generate the two-dimensional image 56 as shown in FIG. 2. The control unit 41 generates the three-dimensional image 53 as shown in FIG. 2 in which the portion specified by the three-dimensional coordinates stored in the storage unit 42 is hidden or transparent. The control unit 41 causes the display 16 to display the generated two-dimensional image 56 and three-dimensional image 53 via the output unit 45.

In the present embodiment, as shown in FIG. 2, the control unit 41 of the image processing device 11 generates, as the two-dimensional image 56, an image in which the region 65 corresponding to the cutting region 62 is represented by a color different from that of a remaining region. For example, a white portion in a general IVUS image may be changed to red in the region 65.

In S118, if there is an operation of setting the cutting region 62 as the change operation by the user, processing in S119 is executed. If there is no change operation by the user, processing in S120 is executed.

In S119, similar to the processing in S112, the control unit 41 of the image processing device 11 receives, via the input unit 44, the operation of setting the cutting region 62. Then, the processing in S115 and the subsequent steps is executed.

In S120, if the tomographic data 51 is updated, processing in S121 and S122 is executed. If the tomographic data 51 is not updated, the presence or absence of the change operation by the user is confirmed again in S118.

In S121, similar to the processing in S101 or S107, the control unit 41 of the image processing device 11 processes the signal input from the probe 20 to newly generate cross-sectional images of the biological tissue 60, thereby acquiring the tomographic data 51 including at least one new cross-sectional image.

In S122, the control unit 41 of the image processing device 11 updates the three-dimensional data 52 of the biological tissue 60 based on the tomographic data 51 acquired in S121. Thereafter, the processing in S113 and the subsequent steps is executed. In S122, it is preferable to update only data at a location corresponding to the updated tomographic data 51. In this case, the data processing amount when generating the three-dimensional data 52 can be reduced, and the real-time property of data processing in S113 and the subsequent steps can be improved.

As described above, in the present embodiment, the control unit 41 of the image processing device 11 causes the display 16 to display, as the three-dimensional image 53, the three-dimensional data 52 representing the biological tissue 60. The control unit 41 forms, in the three-dimensional data 52, the cutting region 62 exposing the lumen 63 of the biological tissue 60 in the three-dimensional image 53. The control unit 41 causes the display 16 to display, together with the three-dimensional image 53, the two-dimensional image 56 representing the cross section 64 of the biological tissue 60 and the region 65 corresponding to the cutting region 62 in the cross section 64.

According to the present embodiment, it is possible to indicate how a part of the structure of the biological tissue 60 is cut out. Therefore, the user can understand based on the two-dimensional image 56, the kind of structure of a portion of the biological tissue 60 that is cut out or omitted and not displayed in the three-dimensional image 53. For example, if the user is an operator, it is relatively easy to perform a treatment for the inside of the biological tissue 60.

In the present embodiment, the control unit 41 of the image processing device 11 generates and updates the three-dimensional data 52 representing the biological tissue 60 based on the tomographic data 51 of the biological tissue 60 acquired by the sensor that acquires the tomographic data 51 while moving through the lumen 63 of the biological tissue 60. The control unit 41 causes the display 16 to display the three-dimensional data 52 as the three-dimensional image 53. The control unit 41 colors, in the three-dimensional image 53, at least the voxel representing the inner surface 61 of the biological tissue 60 or the voxel that is adjacent to the voxel representing the inner surface 61 and that represents the lumen 63 among the first voxel group 54 corresponding to the cross section 64 indicated by the tomographic data 51 newly acquired by the sensor, in a manner of being distinguished from the second voxel group 55 corresponding to the another cross section of the biological tissue 60.

According to the present embodiment, it is possible to indicate which part in the three-dimensional image 53 the cross section 64 of the biological tissue 60 indicated by the tomographic data 51 newly acquired by the sensor corresponds to. Therefore, the user who observes the lumen 63 of the biological tissue 60 using the three-dimensional image 53 can relatively easily understand which part in the three-dimensional image 53 the information currently obtained by the sensor, that is, the latest information corresponds to.

The present disclosure is not limited to the above-described embodiments. For example, two or more blocks described in a block diagram may be integrated, or one block may be divided. Instead of executing two or more steps described in the flowchart in time series according to the description, the steps may be executed in parallel or in a different order according to a processing capability of the device that executes each step or as necessary. In addition, modifications can be made without departing from a gist of the present disclosure.

The detailed description above describes embodiments of an image processing device, an image processing system, an image display method, and an image processing program. The invention is not limited, however, to the precise embodiments and variations described. Various changes, modifications and equivalents may occur to one skilled in the art without departing from the spirit and scope of the invention as defined in the accompanying claims. It is expressly intended that all such changes, modifications and equivalents which fall within the scope of the claims are embraced by the claims.

What is claimed is:

1. An image processing device for causing a display to display, as a three-dimensional image, three-dimensional data representing a biological tissue, the image processing device comprising:

a processor configured to:

acquire tomographic data of the biological tissue obtained by a sensor configured to acquire the tomographic data while moving through a lumen of the biological tissue;

generate the three-dimensional data based on the tomographic data;

cause the display to display a two-dimensional image representing a cross section indicated by the tomographic data;

set, as one point, a centroid position of the cross section represented by the two-dimensional image;

display, on the two-dimensional image, a first straight line and a second straight line that extend from the one point;

accept a first operation by a user of setting a direction of the first straight line from the one point and a second operation by the user of setting an angle formed by the first and second straight lines, thereby setting a two-dimensional cutting region partitioned by the first and second straight lines;

display, on the two-dimensional image, the two-dimensional cutting region by coloring, together with the biological tissue included in the two-dimensional cutting region, the two-dimensional cutting region with a color different from a color of a remaining region, such that the biological tissue within the two-dimensional cutting region remains entirely visible on the two-dimensional image;

set, as cutting planes, two planes that intersect along any line passing through the one point and that respectively include the first and second straight lines;

form, in the three-dimensional data, a three-dimensional cutting region sandwiched between the cutting planes and exposing the lumen of the biological tissue in the three-dimensional image;

set, based on a position of the two-dimensional cutting region, a viewpoint such that the three-dimensional image is displayed on a screen as seen from the viewpoint;

display, according to the position of the two-dimensional cutting region, a virtual camera representing the viewpoint on the two-dimensional image; and cause the display to display on the screen, as the three-dimensional image as seen from the viewpoint, the three-dimensional data in which the three-dimensional cutting region is formed, together with the two-dimensional image on which the two-dimensional cutting region and the virtual camera representing the viewpoint are displayed.

2. The image processing device according to claim 1, wherein the processor is configured to cause the display to display, as the three-dimensional image, a three-dimensional image in which at least a voxel representing an inner surface of the biological tissue or a voxel that is adjacent to the voxel representing the inner surface and that represents the lumen among a first voxel group corresponding to the cross section represented by the two-dimensional image is colored in a manner of being distinguished from a second voxel group corresponding to another cross section of the biological tissue, together with the two-dimensional image.

3. The image processing device according to claim 2, wherein the processor is configured to cause the display to display, as the three-dimensional image, a three-dimensional image in which all of voxels representing the biological tissue among the first voxel group are colored in a manner of being distinguished from the second voxel group, together with the two-dimensional image.

4. An image processing system comprising:

the image processing device according to claim 1;

a probe including the sensor.

5. The image processing system according to claim 4, further comprising the display.

6. The image processing device according to claim 1, wherein the processor is configured to accept, as the first operation, an operation of setting a base angle that is a rotation angle about the one point for the first straight line, and, as the second operation, an operation of setting an opening angle that is the angle formed by the first and second straight lines, thereby setting the two-dimensional cutting region.

7. The image processing device according to claim 1, wherein the processor is configured to cause the display to display, as the two-dimensional image, a latest cross-sectional image corresponding to a current position of the sensor.

8. The image processing device according to claim 1, wherein the processor is configured to, during an operation by the user for changing the position of the two-dimensional cutting region on the two-dimensional image, display the virtual camera on the two-dimensional image at a position corresponding to the position of the two-dimensional cutting region before being changed.

9. An image display method for displaying on a display, as a three-dimensional image, three-dimensional data representing a biological tissue, the image display method comprising:

acquiring, by a processor, tomographic data of the biological tissue obtained by a sensor configured to acquire the tomographic data while moving through a lumen of the biological tissue;

generating, by the processor, the three-dimensional data based on the tomographic data;

displaying, on the display, a two-dimensional image representing a cross section indicated by the tomographic data;

setting, by the processor, as one point, a centroid position of the cross section represented by the two-dimensional image;

displaying, by the processor, on the two-dimensional image, a first straight line and a second straight line that extend from the one point;

accepting, by the processor, a first operation by a user of setting a direction of the first straight line from the one point and a second operation by the user of setting an angle formed by the first and second straight lines, thereby setting a two-dimensional cutting region partitioned by the first and second straight lines;

displaying, by the processor, on the two-dimensional image, the two-dimensional cutting region by coloring, together with the biological tissue included in the two-dimensional cutting region, the two-dimensional cutting region with a color different from a color of a remaining region, such that the biological tissue within the two-dimensional cutting region remains entirely visible on the two-dimensional image;

setting, by the processor, as cutting planes, two planes that intersect along any line passing through the one point and that respectively include the first and second straight lines;

forming, by the processor, in the three-dimensional data, a three-dimensional cutting region sandwiched between the cutting planes and exposing the lumen of the biological tissue in the three-dimensional image;

setting, by the processor, based on a position of the two-dimensional cutting region, a viewpoint such that the three-dimensional image is displayed on a screen as seen from the viewpoint;

displaying, by the processor, according to the position of the two-dimensional cutting region, a virtual camera representing the viewpoint on the two-dimensional image; and displaying on the screen, on the display, as the three-dimensional image as seen from the viewpoint, the three-dimensional data in which the three-dimensional cutting region is formed, together with the two-dimensional image on which the two-dimensional cutting region and the virtual camera representing the viewpoint are displayed.

10. The image display method according to claim 9, further comprising:

displaying, on the display, as the three-dimensional image, a three-dimensional image in which at least a voxel representing an inner surface of the biological tissue or a voxel that is adjacent to the voxel representing the inner surface and that represents the lumen among a first voxel group corresponding to the cross section represented by the two-dimensional image is colored in a manner of being distinguished from a second voxel group corresponding to another cross section of the biological tissue, together with the two-dimensional image.

11. The image display method according to claim 10, further comprising:

displaying, on the display, as the three-dimensional image, a three-dimensional image in which all of voxels representing the biological tissue among the first voxel group are colored in a manner of being distinguished from the second voxel group, together with the two-dimensional image.

12. The image display method according to claim 9, further comprising:

accepting, by the processor, as the first operation, an operation of setting a base angle that is a rotation angle about the one point for the first straight line, and, as the second operation, an operation of setting an opening angle that is the angle formed by the first and second straight lines, thereby setting the two-dimensional cutting region.

13. The image display method according to claim 12, further comprising:

displaying, on the display, as the two-dimensional image, a latest cross-sectional image corresponding to a current position of the sensor.

14. The image display method according to claim 12, further comprising:

during an operation by the user for changing the position of the two-dimensional cutting region on the two-dimensional image, displaying the virtual camera on the two-dimensional image at a position corresponding to the position of the two-dimensional cutting region before being changed.

15. A non-transitory computer readable medium storing an image processing program which, when executed by a computer, causes a display to display, as a three-dimensional image, three-dimensional data representing a biological tissue, and performs, by a processor, processing comprising:

acquiring tomographic data of the biological tissue obtained by a sensor configured to acquire the tomographic data while moving through a lumen of the biological tissue;

generating the three-dimensional data based on the tomographic data;

causing the display to display a two-dimensional image representing a cross section indicated by the tomographic data;

setting, as one point, a centroid position of the cross section represented by the two-dimensional image;

displaying, on the two-dimensional image, a first straight line and a second straight line that extend from the one point;

accepting a first operation by a user of setting a direction of the first straight line from the one point and a second operation by the user of setting an angle formed by the first and second straight lines, thereby setting a two-dimensional cutting region partitioned by the first and second straight lines;

displaying, on the two-dimensional image, the two-dimensional cutting region by coloring, together with the biological tissue included in the two-dimensional cutting region, the two-dimensional cutting region with a color different from a color of a remaining region, such that the biological tissue within the two-dimensional cutting region remains entirely visible on the two-dimensional image;

setting as cutting planes, two planes that intersect along any line passing through the one point and that respectively include the first and second straight lines;

forming, in the three-dimensional data, a three-dimensional cutting region sandwiched between the cutting planes and exposing the lumen of the biological tissue in the three-dimensional image;

setting, based on a position of the two-dimensional cutting region, a viewpoint such that the three-dimensional image is displayed on a screen as seen from the viewpoint;

displaying, according to the position of the two-dimensional cutting region, a virtual camera representing the viewpoint on the two-dimensional image; and causing the display to display on the screen, as the three-dimensional image as seen from the viewpoint, the three-dimensional data in which the three-dimensional cutting region is formed, together with the two-dimensional image on which the two-dimensional cutting region and the virtual camera representing the viewpoint are displayed.

16. The non-transitory computer readable medium according to claim 15, wherein the processing further comprises accepting, as the first operation, an operation of setting a base angle that is a rotation angle about the one point for the first straight line, and, as the second operation, an operation of setting an opening angle that is the angle formed by the first and second straight lines, thereby setting the two-dimensional cutting region.

17. The non-transitory computer readable medium according to claim 15, wherein the processing further comprises causing the display to display, as the two-dimensional image, a latest cross-sectional image corresponding to a current position of the sensor.

18. The non-transitory computer readable medium according to claim 15, wherein the processing further comprises, during an operation by the user for changing the position of the two-dimensional cutting region on the two-dimensional image, displaying the virtual camera on the two-dimensional image at a position corresponding to the position of the two-dimensional cutting region before being changed.

* * * * *